(12) United States Patent
Nomura et al.

(10) Patent No.: US 7,022,823 B2
(45) Date of Patent: Apr. 4, 2006

(54) DIAZONIUM SALT, ITS SYNTHESIZING METHOD AND RECORDING MATERIAL

(75) Inventors: Kimiatsu Nomura, Shizuoka-ken (JP); Hisato Nagase, Shizuoka-ken (JP); Yasuhiro Mitamura, Shizuoka-ken (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 67 days.

(21) Appl. No.: 10/636,816

(22) Filed: Aug. 8, 2003

(65) Prior Publication Data

US 2004/0039180 A1    Feb. 26, 2004

(30) Foreign Application Priority Data

Aug. 22, 2002  (JP) .............................. 2002-241646

(51) Int. Cl.
*C07C 245/20*    (2006.01)
*G03C 1/54*    (2006.01)
*G03F 7/16*    (2006.01)
*B41M 5/165*    (2006.01)

(52) U.S. Cl. ..................... 534/560; 548/161; 548/164; 503/215; 503/218; 430/138; 430/157

(58) Field of Classification Search ................ 548/164, 548/161; 534/560; 503/215, 218; 430/138, 430/157
See application file for complete search history.

(56) References Cited

FOREIGN PATENT DOCUMENTS

| JP | 08-324129 A | 12/1996 |
|---|---|---|
| JP | 11-078232 A | 3/1999 |
| JP | 11-116553 A | 4/1999 |
| JP | 11-228517 A | 8/1999 |
| JP | 2003-321447 A | 11/2003 |

OTHER PUBLICATIONS

Shin Jikken Kagaku Kouza: (New Experimental Chemical Seminar), vol. 14-III (Maruzen Co., Ltd.), pp. 1516-1534, 1978.
Khoji Sato, et al.: in Gazou Denshi Gakkai Shi (Journal of Image Electronics Society) 11, No. 4 (1982): pp. 290-296.
Tomomasa Usami, et al.: in Densi Shasin Gakkai Shi (Journal of Electrographic Society) 26, No. 2 (1987): pp115-119.

*Primary Examiner*—Laura L. Stockton
(74) *Attorney, Agent, or Firm*—Sughrue Mion. PLLC

(57) ABSTRACT

The present invention relates to a diazonium salt represented by the following general formula (1) and a synthesizing method thereof, as well as a recording material using the diazonium salt.

In general formula (1), $R^1$ represents a hydrogen atom, an alkyl group or an aryl group. $R^2$ represents an alkyl group or an aryl group. Each of $R^3$, $R^4$, $R^5$ and $R^6$ independently represents a hydrogen atom or a monovalent substituent. Here, at least one of $R^3$, $R^4$, $R^5$ and $R^6$ represents $-N_2^+X^-$. $X^-$ represents an anion.

General formula (1)

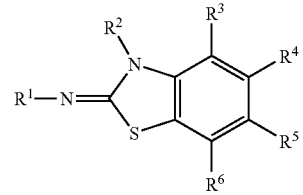

20 Claims, No Drawings

DIAZONIUM SALT, ITS SYNTHESIZING METHOD AND RECORDING MATERIAL

CROSS-REFERENCE TO RELATED APPLICATION

This application claims priority under 35USC 119 from Japanese Patent Application No. 2002-241646, the disclosure of which is incorporated by reference herein.

BACKGROUND OF THE INVENTION

1. Field of the Invention

The present invention relates to diazonium salt and a synthesizing method thereof as well as a recording material. And more particularly, the present invention relates to diazonium salt that is useful as a synthesizing intermediate material of an azo pigment, an analyzing reagent, a raw material for a photosensitive recording material and the like, and a recording material that is superior in photo-fixing property, shelf-stability of raw photosensitive material and light-fastness of the surface of the background.

2. Description of the Related Art

Diazonium salts have been known as an important intermediate in synthesizing an azo pigment. Conventionally, for the synthesis method of the azo pigment, various methods have been known, and as described in *Shin Jikken Kagaku Kouza* (New Experimental Chemical Seminar), vol 14-III (Maruzen Co., Ltd.), pp.1516–1534, there are various synthesizing methods, such as a synthesis employing oxidation, reduction, substitution, addition, or condensation. However, such methods have the risk of an explosion of diazonium salt during synthesis, and there have been strong demands for the development of a stable diazonium salt that reduces the risk of an explosion.

As described in Japanese Patent Application Laid-Open (JP-A) No. 11-228517, the diazonium salt is used for a quantitative analysis of bilirubin that is a main component of the bile pigment contained in body fluid, and considered to be an important compound in medical and pharmaceutical fields as well.

In general, the diazonium salt, which has an extremely high chemical activity, and reacts with a compound referred to as a coupler having a phenol derivative and an active methylene base to easily form an azo dye, and also has a photosensitivity so that it is decomposed upon application of light to lose its activity. For this reason, the diazonium salt has been utilized for a long time as a photo-recording material typically represented by a diazo copying material (see *Shasin Kougakuno Kiso: Higinenshasin hen* (Basics of Photographic Engineering-Non-Silver-Salt Photography—), ed. Japan Photographic Society (Corona Publishing Co., Ltd., 1982), pp. 89–117, 182–201).

In recent years, the diazonium salt is also applied to a recording material capable of fixing an image by utilizing its characteristic of being decomposed by light to lose its activity, and the typical examples include a photo-fixing-type heat-sensitive recording material (proposed by Khoji Sato et al. in *Gazou Denshi Gakkai Shi* (Journal of Image Electronics Society) 11, no. 4 (1982): pp. 290–296) in which a recording material bearing a recording layer containing diazonium salt and a coupler is heated and allowed to react in accordance with an image signal to form an image, then the image is fixed with light irradiation.

These recording materials using the diazonium salt as a color-developing component has the disadvantage which resulting in a short shelf life as a recording material since the diazonium salt has an extremely high chemical activity, and is thermally decomposed gradually even in a dark place to lose its reactivity, Moreover, another disadvantage is that the generation of colored decomposed materials (stains) causes the non-image portion to be colored, since the residual diazonium salt compound is decomposed at a portion exposing the background that is a non-image portion, at photo-fixing. Furthermore, also in the finished image after the fixing process, the non-image portion has a poor light-fastness, and the coloring is enhanced when left under sun light or fluorescent light for a long time.

Improvement of the recording speed has been studied for a long time as a problem to be solved, and there have been strong demands for diazonium salt having an improved photo-fixing property and capable of carrying out a photo-fixing process for a short time.

As a means for solving such a problem of instability of the diazonium salt, various methods have been proposed. Among these, one of the most effective means is to encapsulate diazonium salt in microcapsules. By forming the microcapsules containing diazonium salt, the diazonium salt is separated from substances such as water and bases that accelerate the decomposition thereof, with the result that the decomposition is effectively reduced and it becomes possible to extremely improve the shelf life of a recording material using the diazonium compound (proposed by Tomomasa Usami, et al. in *Densi Shasin Gakkai shi* (Journal of Electrophotographic Society) 26, no. 2 (1987): pp. 115–119).

In the general method for encapsulating diazonium salt in microcapsules, diazonium salt is dissolved in a hydrophobic solvent (oil phase) and this solution is added to an aqueous solution (water phase) in which a water-soluble polymer has been dissolved, and emulsified and dispersed by a homogenizer or the like, while a monomer or a prepolymer to be used for forming a wall material of microcapsules is added to either the oil phase or the water phase, or to both of the phases so that a polymerizing reaction is allowed to take place in the interface between the oil phase and the water phase, or a polymer is deposited on the interface to form a wall made from the polymer compound; thus, microcapsules are formed. This method is described in detail in, for example, Asashi Kondo, *Maikuro Kapuseru* (Microcapsule) (Nikkan Kogyo Shimbun Ltd., 1970) and Tamotsu Kondo, et al. *Maikuro Kapuseru* (Microcapsule) (Sankyo Publishing Company, 1977).

The capsule wall of the microcapsules to be formed employs various materials, such as cross-linking gelatin, alginate, celluloses, urea resin, urethane resin, melamine resin and nylon resin.

In particular, in the case of microcapsules having walls having a glass transition temperature slightly higher than room temperature, such as those made of urea resin or urethane resin, the capsule wall is impermeable to substances at room temperature and permeable to substances at or higher than the glass transition temperature. Therefore, these microcapsules are referred to as thermal responsive microcapsules, which are effectively used as the recording material of a heat sensitive system.

In other words, in the case when a heat sensitive recording material is formed which has a heat sensitive recording layer comprising heat responsive microcapsules containing diazonium salt and a coupler placed outside the capsules as a main component of color-development, it is possible to maintain the diazonium salt stable for a long time, to easily form a color-developed image by applying heat thereto, and also to carry out a fixing process on the image thus formed by applying light thereto.

Therefore, it becomes possible to extremely improve the stability as the recording material by encapsulating diazonium salt into microcapsules.

As described above, although it has become possible to extremely improve the stability as the heat sensitive recording material, the instability in diazonium salt is not completely eliminated and the heat sensitive recording material and the like comprising the diazonium salt in the microcapsule have not achieved a sufficient long-term shelf life. Moreover, even after printing and fixing, when exposed to a light source for a long time, the photo-decomposing substance of the diazonium salt tends to have a photo-decomposing reaction, with the result that colored stains increase following the reaction, causing degradation in the degree of whiteness in the non-image portion (background portion) after the photo-fixing process and the subsequent reduction in the contrast with the colored portion.

Moreover, it has been known that the photo-decomposing reaction does not take place evenly to cause various decomposition products depending on ambient environments and the like; thus, among those matters of several tens of kinds or more, in particular, there are products having an absorbing range in a visible range, which are referred to as photo-decomposition stains. Here, when the stains are generated extremely, there is degradation in the degree of whiteness in the non-image portion (background portion) after the photo-fixing process, and the subsequent reduction in the contrast with the color-developing portion; consequently, the commercial value of the recording material is extremely impaired.

Here, since the photo-decomposition of the diazonium salt is complicated, and it is difficult to specify the resultant products, it has been considered that the reduction of the photo-decomposition stains is difficult.

Therefore, in recent years, with respect to improvements in the long-term stability by reducing the photo-decomposition stains, various researches have been made, and, for example, JP-A No. 8-324129 has proposed a photo-fixing-type heat sensitive recording material which is formed by using a specific hydrophobic oil in combination with microcapsules containing a photo-fixing-type diazonium salt so that it has a superior property in the raw shelf life, and is consequently less susceptible to degradation in the degree of whiteness even upon exposure to light for a long time after an image-forming process and also superior in image shelf-stability. Moreover, JP-A No. 11-78232 has proposed a non-fixing-type heat sensitive recording material using a novel diazonium salt in an attempt to improve the stability of the diazonium salt itself. In other words, a diazonium salt having the maximum light-absorbing wavelength in a shorter wavelength range than the proximity of 350 nm is contained in microcapsules, and by using a non-fixing-type heat sensitive recording material using these microcapsules, the proposed material can improve the degree of whiteness in the background portion and the image shelf life, after formation of an image with a light source having longer wavelengths than the proximity of 350 nm, generally exemplified by a general-use fluorescent lamp or the like.

However, at present, the raw material shelf life and the image shelf life in colored portions and background portions (non-image portions) after an image-recording process have been still insufficient, and there have been demands for further improvements in the stability.

Moreover, in recent years, there have been demands for shortened recording time required for the image recording process, that is, demands for high-speed image forming processes including printing and fixing processes. In particular, regarding the photo-fixing-type heat sensitive recording material using the diazonium salt, there have been strong demands for techniques that can achieve high-speed processes while improving the stability as described above, and in an attempt to satisfy the demands, it is essential to improve the photo-decomposing speed of the diazonium salt.

These recording materials using the diazonium salt as a color-developing component are generally arranged so that ultraviolet rays having wavelengths of approximately 360 nm are irradiated in the fixing process in order to effectively carry out the photo-fixing process. However, since the ultraviolet rays require a special light source and tend to give adverse effects to the eyes, there have been demands for a recording material using diazonium salt that can be effectively fixed by a light source that emits visible light rays having long wavelengths exceeding 400 nm.

However, recording materials using conventional diazonium salt raise a problem in that upon deactivating the diazonium salt by using a light source having a long wavelength of 400 nm or over, the fixing process becomes slower and takes a long time. Moreover, when a photo-fixing process is carried out for a long time in an attempt to completely carry out the fixing process, generated products by the fixing process are allowed to further react to cause degradation in the degree of surface whiteness in a color-developed image.

Moreover, in JP-A No. 11-116553 and Japanese Patent Application No. 2002-131575, the inventors, etc. of this invention have proposed a novel diazonium salt having the maximum absorption wavelength (λmax) over 400 nm (that is, 4-indolino-type diazonium salt in which a substituent on an aromatic ring of a heterocyclic structural portion containing nitrogen, is a hydrogen atom, an alkyl group, an alkoxy group, a halogen group, an acyl group or an acyl amino group); however, in the heat sensitive recording material comprising the diazonium salt as a color-developing component, there have been further demands for improvements particularly in the prevention of coloring of background portion after the photo-fixing process.

SUMMARY OF THE INVENTION

The object of the present invention is to solve the conventional problems, and to achieve the following.

In other words, the first object of the invention is to provide a novel diazonium salt and a synthesizing method thereof. The second object of the invention is to provide a recording material which has a fixing sensitivity to light having wavelengths of 400 to 500 nm, and is superior in the photo-fixing property, shelf-stability of raw photosensitive material and light-fastness of the background.

As a result of earnest studies to solve the problems, the present inventors have successfully synthesized a novel diazonium salt that has benzothiazoline as its core region, and found that a recording material containing the diazonium salt is superior in the photo-fixing property, shelf-stability of raw photosensitive material and light-fastness of the background; thus, the present invention is completed.

In other words, the problems can be solved by the invention through the following means:

The first aspect of the invention is to provide a diazonium salt (K) represented by the following general formula (1):

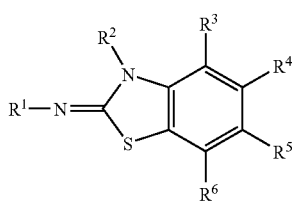

General formula (1)

wherein in general formula (1), $R^1$ represents a hydrogen atom, an alkyl group or an aryl group; $R^2$ represents an alkyl group or an aryl group; $R^3$, $R^4$, $R^5$ and $R^6$ each independently represent a hydrogen atom or a monovalent substituent, and at least one of $R^3$, $R^4$, $R^5$ and $R^6$ represents $-N_2^+X^-$, in which $X^-$ represents an anion.

The second aspect of the invention is to provide a diazonium salt (K), wherein in general formula (1), at least one of $R^1$ and $R^2$ represents an alkyl group having 1 to 30 total carbon atoms which may have a substituent, or an aryl group having 6 to 30 total carbon atoms which may have a substituent.

The third aspect of the invention is to provide a diazonium salt (K), wherein in general formula (1), at least one of $R^1$ and $R^2$ is selected from the group consisting of an ethyl group, a butyl group, a hexyl group, a benzyl group, an N,N-diethylcarbamoylmethyl group, a 1-(N,N-dibutylcarbamoyl) ethyl group, a 1-methyl-2-phenoxyethyl group, a (4-chlorophenyl) methyl group and a (2,4-dichlorophenyl) methyl group.

The fourth aspect of the invention is to provide a diazonium salt (K), wherein in general formula (1), $R^3$, $R^4$, $R^5$ and $R^6$ each independently represent a hydrogen atom, a halogen atom, an alkyl group, an aryl group, an alkoxy group, an aryloxy group, an alkyl thio group, an aryl thio group, an alkyl sulfonyl group, an aryl sulfonyl group, an acyl amino group, a sulfonyl amino group, or $-N_2^+X^-$.

The fifth aspect of the invention is to provide a diazonium salt (K), wherein in general formula (1), $R^3$ and $R^6$ each independently represent a hydrogen atom, a halogen atom, an alkyl group, an aryl group, an alkoxy group, an aryloxy group, an alkyl thio group, an aryl thio group, an alkyl sulfonyl group, an aryl sulfonyl group, an acyl amino group, a sulfonyl amino group, or $-N_2^+X^-$, $R^5$ represents $-N_2^+X^-$, and $R^4$ represents an alkoxy group or an aryloxy group.

The sixth aspect of the invention is to provide a diazonium salt (K), wherein in general formula (1), at least one of $R^1$ to $R^7$ has a diazonio aryl group acting as a substituent.

The seventh aspect of the invention is to provide a recording material (L) containing a diazonium salt represented by the general formula (1).

The eighth aspect of the invention is to provide a recording material (L), wherein a heat sensitive recording layer containing the diazonium salt represented by general formula (1) and a coupler is provided on a support.

The nineth aspect of the invention is to provide a recording material (L), wherein a heat sensitive recording layer containing the diazonium salt represented by general formula (1) and a coupler is provided on a support and the coupler is a compound represented by the following general formula (2) or a tautomer thereof:

$$E^1-CH_2-E^2$$ General formula (2)

wherein in general formula (2), $E^1$ and $E^2$ each independently represent an electron-attractive group, and $E^1$ and $E^2$ may be bonded to each other to form a ring.

The tenth aspect of the invention is to provide a recording material (L) further comprising an organic base, wherein a heat sensitive recording layer containing the diazonium salt represented by general formula (1) and a coupler is provided on a support.

The eleventh aspect of the invention is to provide a recording material (L) further comprising an organic base, wherein a heat sensitive recording layer containing the diazonium salt represented by general formula (1) and a coupler is provided on a support, and the content of the organic base is from 0.1 to 30 parts by mass per 1 mass part of the diazonium salt.

The twelfth aspect of the invention is to provide a recording material (L), wherein a heat sensitive recording layer containing the diazonium salt represented by general formula (1) and a coupler is provided on a support, and in the heat sensitive recording layer, the content of the diazonium salt represented by general formula (1) is from 0.02 to 5 $g/m^2$.

The thirteenth aspect of the invention is to provide a recording material (L), wherein a heat sensitive recording layer containing the diazonium salt represented by general formula (1), a coupler, and a color-developing assistant, is provided on a support.

The fourteenth aspect of the invention is to provide a recording material (L), wherein a heat sensitive recording layer containing the diazonium salt represented by general formula (1), a coupler, and a radical generating agent, is provided on a support.

The fifteenth aspect of the invention is to provide a recording material (L), wherein a heat sensitive recording layer containing the diazonium salt represented by general formula (1), a coupler, and a vinyl monomer, is provided on a support.

The sixteenth aspect of the invention is to provide a recording material (L), wherein a heat sensitive recording layer containing the diazonium salt represented by general formula (1), a coupler, and an antioxidant, is provided on a support.

The seventeenth aspect of the invention is to provide a recording material (L), wherein a heat sensitive recording layer containing the diazonium salt represented by general formula (1) and a coupler is provided on a support, and the diazonium salt is contained in microcapsules.

The eighteenth aspect of the invention is to provide a recording material (L), wherein a heat sensitive recording layer containing the diazonium salt represented by general formula (1) and a coupler is provided on a support, the diazonium salt is contained in microcapsules, and capsule walls of the microcapsules contain at least one of polyurethane and polyurea as a constituent component.

The nineteenth aspect of the invention is to provide a recording material (L), wherein a heat sensitive recording layer containing the diazonium salt represented by general formula (1) and a coupler is provided on a support, and the recording material is photo-fixed by using a light source having a light-emission center wavelength of 380 to 460 nm.

The twentieth aspect of the invention is to provide a method for synthesizing a diazonium salt, wherein a compound represented by the following general formula (3) is used as a raw material:

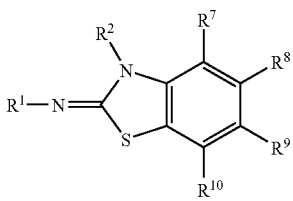

General formula (3)

wherein in general formula (3), $R^1$ represents a hydrogen atom, an alkyl group or an aryl group; $R^2$ represents an alkyl group or an aryl group; $R^7$, $R^8$, $R^9$ and $R^{10}$ each independently represent a hydrogen atom or a monovalent substituent, and at least one of $R^7$, $R^8$, $R^9$ and $R^{10}$ represents —$NHR^{11}$, in which $R^{11}$ represents a hydrogen atom or an acyl group.

DETAILED DESCRIPTION OF THE INVENTION

The following description will discuss a diazonium salt of the present invention and a synthesizing method thereof as well as a recording material using the diazonium salt in detail.

<Diazonium Salt>

The diazonium salt of the invention is represented by the following general formula (1):

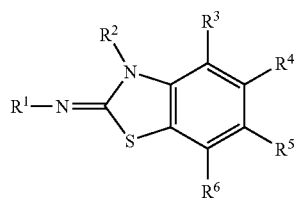

General formula (1)

In general formula (1), $R^1$ represents a hydrogen atom, an alkyl group or an aryl group. $R^2$ represents an alkyl group or an aryl group. Each of $R^3$, $R^4$, $R^5$ and $R^6$ independently represents a hydrogen atom or a monovalent substituent. Wherein, at least one of $R^3$, $R^4$, $R^5$ and $R^6$ represents —$N_2^+X^-$. $X^-$ represents an anion.

The alkyl group represented by $R^1$ may have no substituent or have a substituent, and as the substituent to be introduced into the alkyl group, preferable examples thereof include: an aryl group, a halogen atom, an alkoxy group, an aryloxy group, an alkoxy carbonyl group, an acyloxy group, an acylamino group, a carbamoyl group, a cyano group, a carboxyl group, a sulfonyl group and a heterocyclic residue.

The alkyl group represented by $R^1$ is preferably an alkyl group having 1 to 30 total carbon atoms, more preferably, an alkyl group having 1 to 20 total carbon atoms. More specifically, preferable examples thereof include: a methyl group, an ethyl group, a butyl group, a hexyl group, an octyl group, a 2-ethylhexyl group, a 3,5,5-trimethylhexyl group, a dodecyl group, an octadecyl group, a benzyl group, a (4-ethoxyphenyl) methyl group, an N,N-diethyl carbamoyl methyl group, an N,N-dibutyl carbamoyl methyl group, a 1-(N,N-dibutyl carbamoyl) ethyl group, a 2-methoxy ethyl group, a 1-methyl-2-phenoxyethyl group, a (4-chlorophenyl) methyl group and a (2,4-dichlorophenyl) methyl group, and more preferable examples are an ethyl group, a butyl group, a hexyl group, a benzyl group, an N,N-diethyl carbamoyl methyl group, an N,N-dibutyl carbamoyl methyl group, a 1-(N,N-dibutyl carbamoyl) ethyl group, a 1-methyl-2-phenoxyethyl group, a (4-chlorophenyl) methyl group and a (2,4-dichlorophenyl) methyl group.

The aryl group represented by $R^1$ may have no substituent or have a substituent, and as the substituent to be introduced into the alkyl group, preferable examples thereof include: an alkyl group, a halogen atom, an alkoxy group, an aryloxy group, an alkoxy carbonyl group, an acyloxy group, an acyl amino group, a carbamoyl group, a cyano group, a carboxyl group, a sulfonyl group and a heterocyclic residue.

The aryl group represented by R1 is preferably an aryl group having 6 to 30 total carbon atoms, more preferably, an aryl group having 6 to 20 total carbon atoms. More specifically, preferable examples thereof include: a phenyl group, a 2-methylphenyl group, a 3-methylphenyl group, a 4-methylphenyl group, a 4-phenylphenoxy group, a 4-chlorophenyl group, a 2-methoxyphenyl group, a 3-ethoxyphenyl group, a 4-butoxyphenyl group, a 2,4-diethoxyphenyl group, a 2,5-dibutoxyphenyl group, a 4-phenoxyphenyl group, a naphthyl group, a 4-dibutyl carbamoyl phenyl group and a 4-dibutyl sulfamoyl phenyl group, and more preferable examples are a phenyl group, a 2-methylphenyl group, a 3-methylphenyl group, a 4-methylphenyl group, a 4-chlorophenyl group, a 2-methoxyphenyl group, a 3-ethoxyphenyl group and a 4-butoxyphenyl group.

$R^2$ represents an alkyl group or an aryl group, and represents the same alkyl group or aryl group as that described in the case of foregoing $R^1$, with preferable specific examples being the same as described for $R^1$.

Each of $R^3$, $R^4$, $R^5$ and $R^6$ independently represents a hydrogen atom or a monovalent substituent. Further, at least one of $R^3$, $R^4$, $R^5$ and $R^6$ represents —$N_2^+X^-$. Here, —$N_2^+$ represents a diazonio group, and $X^-$ represents an anion.

As the monovalent substituent represented by each of $R^3$, $R^4$, $R^5$ and $R^6$, preferable examples thereof include: an alkyl group, an aryl group, a halogen atom, an alkoxy group, an aryloxy group, an alkyl thio group, an aryl thio group, an acyl amino group, an alkoxy carbonyl group, a carbamoyl group, a cyano group, an alkyl sulfonyl group, an aryl sulfonyl group and a sulfamoyl group, and more preferable examples thereof are: a halogen atom, an alkyl group, an aryl group, an alkoxy group, an aryloxy group, an alkyl thio group, an aryl thio group, an acyl amino group, a sulfonyl amino group or —$N_2^+X^-$, and as described above, at least one of $R^3$, $R^4$, $R^5$ and $R^6$ represents —$N_2^+X^-$.

The alkyl groups and aryl groups represented by $R^3$, $R^4$, $R^5$ and $R^6$ are the same as those described for foregoing $R^1$, with preferable specific examples being the same as described for $R^1$.

As the halogen atom represented by $R^3$, $R^4$, $R^5$ or $R^6$, preferable examples include a fluorine atom, a chlorine atom, a bromine atom and an iodine atom, and more preferable examples are a fluorine atom and a chlorine atom.

The alkoxy group, represented by each of $R^3$, $R^4$, $R^5$ or $R^6$, may have no substituent or have a substituent, and is preferably an alkoxy group having 1 to 30 total carbon atoms, more preferably, an alkoxy group having 1 to 20 total carbon atoms. More specifically, preferable examples thereof include: a methoxy group, an ethoxy group, a propoxy group, a butoxy group, a hexyloxy group, a 2-ethylhexyloxy group, a 3,5,5-trimethyl hexyloxy group, an octyloxy group, a decyloxy group, a 2-phenoxyethoxy group, a 2-(3,5-di-t-butylphenoxy) ethoxy group, a dibutyl carbamoyl methoxy group, a hexadecyloxy group and an octadecyloxy group, and more preferable examples are a methoxy group, an ethoxy group, a butoxy group, a hexyloxy group, a 2-ethyl hexyloxy group, a 3,5,5-trimethyl hexyloxy group, a 2-phenoxyethoxy group and a dibutyl carbamoyl methoxy group.

The aryloxy group, represented by $R^3$, $R^4$, $R^5$ or $R^6$, may have no substituent or have a substituent, and is preferably an aryloxy group having 6 to 30 total carbon atoms, more preferably, an aryloxy group having 6 to 20 total carbon atoms. More specifically, preferable examples thereof include: a phenoxy group, a tolyloxy group, a 4-chlorophenyloxy group, a 4-acetamide phenyloxy group, a 2-butoxyphenyloxy group, a 2-benzoyl aminophenyloxy group, a 2,5-dimethoxy-4-nitrophenyloxy group and a 3-octyloxy phenyloxy group, and more preferable groups are a phenoxy group, a tolyloxy group, a 4-chlorophenyloxy group, a 4-acetamide phenyloxy group, a 2-butoxyphenyloxy group and a 2,5-dimethoxy-4-nitrophenyloxy group.

The alkyl thio group, represented by $R^3$, $R^4$, $R^5$ or $R^6$, may have no substituent or have a substituent, and is preferably an alkyl thio group having 1 to 30 total carbon atoms, more preferably, an alkyl thio group having 1 to 20 total carbon atoms. More specifically, preferable examples thereof include: a methylthio group, an ethylthio group, a butylthio group, a hexylthio group, a 2-ethylhexylthio group, a 3,5,5-trimethylhexylthio group, an octylthio group, a decylthio group, a 2-phenoxyethylthio group, a 2-(3,5-di-t-butylphenoxy) ethylthio group, a dibutyl carbamoyl methylthio group, a hexadecylthio group and an octadecylthio group, and more preferable examples are a methylthio group, an ethylthio group, a butylthio group, a hexylthio group, a 2-ethylhexylthio group, a 3,5,5-trimethylhexylthio group, a 2-phenoxyethylthio group and a dibutyl carbamoyl methylthio group.

The aryl thio group, represented by $R^3$, $R^4$, $R^5$ or $R^6$, may have no substituent or have a substituent, and is preferably an aryl thio group having 6 to 30 total carbon atoms, more preferably, an aryl thio group having 6 to 20 total carbon atoms. More specifically, preferable examples thereof include: a phenylthio group, a tolylthio group, a 4-chlorophenylthio group, a 4-acetamide phenylthio group, a 2-butoxyphenylthio group, a 2-benzoyl aminophenylthio group, a 2,5-dimethoxy-4-nitrophenylthio group, a 3-octyloxy phenylthio group, and more preferable examples are a phenylthio group, a tolylthio group, a 4-chlorophenylthio group, a 4-acetamide phenylthio group, a 2-butoxyphenylthio group and a 2,5-dimethoxy-4-nitrophenylthio group.

The acyl amino group, represented by $R^3$, $R^4$, $R^5$ or $R^6$, may have no substituent or have a substituent, and is preferably an acyl amino group having 1 to 30 total carbon atoms, more preferably, an acyl amico group having 1 to 20 total carbon atoms. More specifically, preferable examples thereof include: a formyl amino group, an acetyl amino group, a butyryl amino group, a lauroyl amino group, a benzoyl amino group, a toluoyl amino group, a phenoxy acetyl group, a (4-methoxyphenoxy) acetyl group, a 2',4'-dichlorobenzoyl amino group, a 2',4'-di-t-amylbenzoyl amino group, an acetylmethyl amino group, a benzoylmethyl amino group and an acetylbenzyl amino group, and more preferable examples are an acetyl amino group, a butyryl amino group, a benzoyl amino group, a toluoyl amino group, a phenoxyacetyl group, a 2',4'-di-t-amylbenzoyl amino group, an acetylmethyl amino group, a benzoylmethyl amino group and an acetylbenzyl amino group.

The alkoxy carbonyl group, represented by $R^3$, $R^4$, $R^5$ or $R^6$, may have no substituent or have a substituent, and is preferably an alkoxy carbonyl group having 2 to 30 total carbon atoms, more preferably, an alkoxy carbonyl group having 2 to 20 total carbon atoms. More specifically, preferable examples thereof include: a methoxy carbonyl group, an ethoxy carbonyl group, a butoxy carbonyl group, a phenoxy carbonyl group, a (2-ethylhexyl) oxycarbonyl group, a hexyloxy carbonyl group, an octyloxy carbonyl group, a (4-methoxyphenyl) oxycarbonyl group, and more preferable examples are a methoxy carbonyl group, an ethoxy carbonyl group, a butoxy carbonyl group and a phenoxy carbonyl group.

The carbamoyl group, represented by $R^3$, $R^4$, $R^5$ or $R^6$, may have no substituent or have a substituent, and is preferably a carbamoyl group having 1 to 30 total carbon atoms, more preferably, a carbamoyl group having 1 to 20 total carbon atoms. More specifically, preferable examples thereof include: a carbamoyl group, an N-phenyl carbamoyl group, an N-butyl carbamoyl group, an N-octyl carbamoyl group, an N,N-dimethyl carbamoyl group, an N,N-diethyl carbamoyl group, an N,N-dibutyl carbamoyl group, an N,N-dihexyl carbamoyl group, an N,N-diphenyl carbamoyl group, an N-methyl-N-phenyl carbamoyl group, an N-ethyl-N-phenyl carbamoyl group, an N-methyl-N-tolyl carbamoyl group, a morpholino carbonyl group, a piperidino carbonyl group and an N,N-bis (2-methoxyethyl) carbamoyl group, and more preferable examples are an N-butyl carbamoyl group, an N-octyl carbamoyl group, an N-phenyl carbamoyl group, an N,N-diethyl carbamoyl group, an N,N-dibutyl carbamoyl group and an N-methyl-N-phenyl carbamoyl group.

The alkyl sulfonyl group, represented by $R^3$, $R^4$, $R^5$ or $R^6$, may have no substituent or have a substituent, and is preferably an alkyl sulfonyl group having 1 to 30 total carbon atoms, more preferably, an alkyl sulfonyl group having 1 to 20 total carbon atoms. More specifically, preferable examples thereof include: a methyl sulfonyl group, an ethyl sulfonyl group, a butyl sulfonyl group, a hexyl sulfonyl group and a benzyl sulfonyl group, and more preferable examples are a methyl sulfonyl group and a benzyl sulfonyl group.

The aryl sulfonyl group, represented by $R^3$, $R^4$, $R^5$ or $R^6$, may have no substituent or have a substituent, and is preferably an aryl sulfonyl group having 1 to 30 total carbon atoms, more preferably, an aryl sulfonyl group having 1 to 20 total carbon atoms. More specifically, preferable examples thereof include: a phenyl sulfonyl group, a 4-methylphenyl sulfonyl group, a naphthyl sulfonyl group, a 4-methoxy sulfonyl group and a 4-chlorophenyl sulfonyl group, and more preferable example are a methyl sulfonyl group, a phenyl sulfonyl group and a 4-methylphenyl sulfonyl group.

The sulfamoyl group, represented by $R^3$, $R^4$, $R^5$ or $R^6$, may have no substituent or have a substituent, and is preferably a sulfamoyl group having 1 to 30 total carbon atoms, more preferably, a sulfamoyl group having 1 to 20 total carbon atoms. More specifically, preferable examples thereof include: a sulfamoyl group, an N-phenyl sulfamoyl group, an N,N-dimethyl sulfamoyl group, an N,N-diethyl sulfamoyl group, an N,N-dibutyl sulfamoyl group, an N,N-dihexyl sulfamoyl group, an N,N-diphenyl sulfamoyl group, an N-methyl-N-phenyl sulfamoyl group, an N-ethyl-N-phenyl sulfamoyl group, an N-methyl-N-tolyl sulfamoyl group, a morpholino sulfonyl group, a piperidino sulfonyl group and an N,N-bis (2-methoxyethyl) sulfonyl group, and more preferable examples are a sulfamoyl group, an N-phenyl sulfamoyl group, an N,N-dibutyl sulfamoyl group, an N,N-diphenyl sulfamoyl group and an N-methyl-N-phenyl sulfamoyl group.

In general formula (1), preferably, at least one of $R^3$, $R^4$, $R^5$ and $R^6$ is an alkoxyl group or an aryloxy group. These alkoxyl group and aryloxy group are the same as those described above, and preferable examples are also the same as those described above. Moreover, as the substituting position, $R^4$ is preferably an alkoxy group or an aryloxy group.

Moreover, at least one of $R^3$, $R^4$, $R^5$ and $R^6$ represents —$N_2^+X^-$; and more preferably, $R^5$ is —$N_2^+X^-$.

As the anion represented by the $X^-$, an inorganic anion or an organic anion may be used. Examples of the inorganic anion include: hexafluorophosphate ion, boron hydrofluoric acid ion, chloride ion and sulfate ion, and among these, hexafluorophosphate ion and boron hydrofluoric acid ion are more preferably used. As the organic anion, preferable examples thereof include: polyfluoro alkyl carboxylic acid ion, polyfluoro alkyl sulfonic acid ion, aromatic carboxylic acid ion, aromatic sulfonic acid ion and ions described in Japanese Patent Application No. 2002-108919, and among these, polyfluoro alkyl carboxylic acid ion, polyfluoro alkyl sulfonic acid ion and ions described in Japanese Patent Application No. 2002-108919 are more preferably used.

Moreover, as the diazonium salt represented by general formula (1), $R^1$, $R^2$, $R^3$, $R^4$, $R^5$, $R^6$ and $R^7$ each may have a diazonio aryl group as a substituent, and each may also have a plurality of diazonio groups.

The diazonium salt represented by general formula (1) of the invention may be obtained by a synthesizing method that will be described later.

Specific examples (exemplary compounds A-1 to A-30) of the diazonium salt represented by general formula (1) is shown in the following; however, the invention is not intended to be limited by these.

A-1

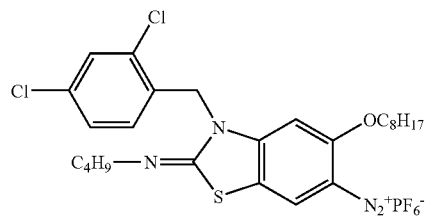

A-5

A-2

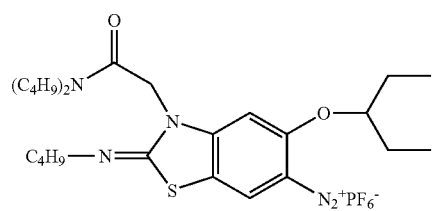

A-6

A-3

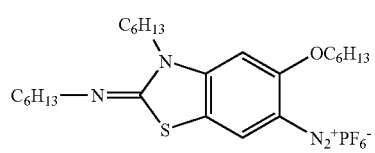

A-7

A-4

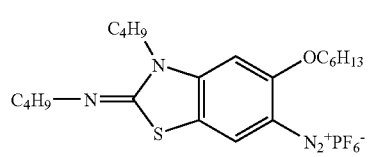

A-8

-continued

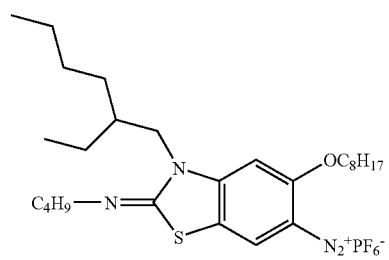

A-9

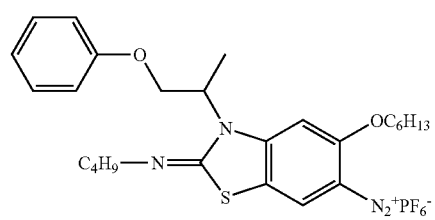

A-10

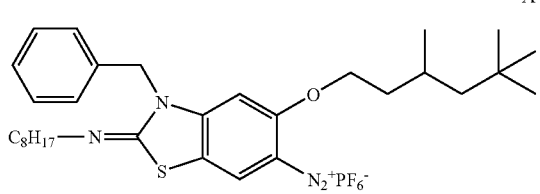

A-11

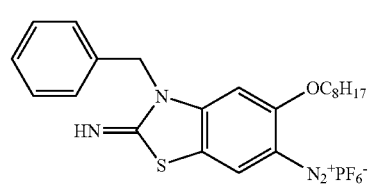

A-12

-continued

A-13, A-14, A-15, A-16, A-17, A-18, A-19, A-20, A-21, A-22, A-23, A-24, A-25, A-26, A-27

-continued

A-28

[Structure: benzyl-N, C4H9-N=, benzothiazole with OC8H17 and N2+C8F17SO3-]

A-29

[Structure: benzyl-N, C4H9-N=, benzothiazole with OC8H17 and N2+, plus separate SO3- on phenyl with C2H5O2C and CO2C2H5]

A-30

[Structure: C6H13-N, C6H13-N=, benzothiazole with OC6H13 and N2+CF3SO2N-SO2CF3]

<Synthesizing Method of Diazonium Salt>

The synthesizing method of diazonium salt recited in the invention is characterized by using a compound represented by the following general formula (3) as a raw material. By the method, the diazonium salt represented by the general formula (1) of the invention is obtained.

General formula (3)

[Structure: benzothiazole with R1—N=, R2 on N, and R7, R8, R9, R10 on benzene ring]

In general formula (3), $R^1$ represents a hydrogen atom, an alkyl group or an aryl group. $R^2$ represents an alkyl group or an aryl group. Each of $R^7$, $R^8$, $R^9$ and $R^{10}$ independently represents a hydrogen atom or a monovalent substituent. Further, at least one of $R^7$, $R^8$, $R^9$ and $R^{10}$ represents —$NHR^{11}$. Here, $R^{11}$ represents a hydrogen atom or an acyl group.

In general formula (3), the alkyl group or the aryl group, represented by $R^1$ or $R^2$, is the same alkyl group or an aryl group as $R^1$ and $R^2$ in the general formula (1), with the preferable examples thereof being the same as those for $R^1$ and $R^2$ in the general formula (1).

In general formula (3), as the monovalent substituent in $R^7$, $R^8$, $R^9$ and $R^{10}$, preferable examples include: an alkyl group, an aryl group, a halogen atom, an alkoxy group, an aryloxy group, an alkyl thio group, an aryl thio group, an acyl amino group, an alkoxy carbonyl group, a carbamoyl group, a cyano group, an alkyl sulfonyl group, an aryl sulfonyl group and a sulfamoyl group, and more preferable examples are a halogen atom, an alkyl group, an aryl group, an alkoxy group, an aryloxy group, an alkyl thio group, an aryl thio group, an acyl amino group, a sulfonyl amino group or —$NHR^{11}$, and as described above, at least one of $R^7$, $R^8$, $R^9$ and $R^{10}$ represents —$NHR^{11}$.

In the case when $R^7$, $R^8$, $R^9$ or $R^{10}$ in general formula (3) represents an alkyl group, an aryl group, a halogen atom, an alkoxy group, an aryloxy group, an alkyl thio group, an aryl thio group, an acyl amino group, an alkoxy carbonyl group, a carbamoyl group, a cyano group, an alkyl sulfonyl group, an aryl sulfonyl group or a sulfamoyl group, $R^7$, $R^8$, $R^9$ or $R^{10}$ represents the same as described in the case of the general formula (1), with the preferable examples thereof also being the same.

In general formula (3), at least one of $R^7$, $R^8$, $R^9$ and $R^{10}$ represents —$NHR^{11}$, and $R^7$ represents a hydrogen atom or an acyl group.

As the acyl group represented by $R^{11}$, an acyl group having 1 to 30 total carbon atoms is preferably used, and an acyl group having 1 to 20 total carbon atoms is more preferably used. Specific preferable examples include: a formyl group, an acetyl group, a propionyl group, a pivaloyl group, a butyloyl group, a 4-phenoxy butyloyl group, a benzoyl group, a (4-ethoxyphenyl) carbonyl group, a (2-buthoxyphenyl) carbonyl group and a (4-chlorophenyl) carbonyl group, and more preferable examples are a formyl group, an acetyl group, a propionyl group, a pivaloyl group, a benzoyl group and a (4-chlorophenyl) carbonyl group.

In the case when any one of $R^7$, $R^8$, $R^9$ and $R^{10}$ in general formula (3) is an amino group, the compound represented by the general formula (3) may form a salt with an acid. Preferable examples of acids are hydrochloric acid, sulfuric acid, methane sulfonic acid and toluene sulfonic acid.

In the case when, upon synthesizing a diazonium salt, $R^7$, $R^8$, $R^9$ and $R^{10}$ in general formula (3) is represented by —$NHR^7$ ($R^7$=an acyl group), this is converted to —$NHR^{11}$ ($R^{11}$=a hydrogen atom) and used. This conversion can be carried out under either an acidic condition or a basic condition, and as an acid to be added, preferable examples thereof include hydrochloric acid, sulfuric acid, alkyl sulfonic acid and aryl sulfonic acid, and as the base to be added, preferable examples thereof include sodium hydroxide, potassium hydroxide and calcium hydroxide. A compound that generates an acid when added is preferably used, and, for example, acetyl chloride and propionyl chloride are preferably used.

As the reaction solvent, preferable examples thereof include water, methanol, ethanol, propanol, butanol and acetic acid, and a mixed solution of these may also be preferably used.

The reaction temperature is preferably set in a range from room temperature to the boiling temperature of the solvent, and from the viewpoint of the reaction speed and solubility, it is preferably set to a high temperature of 50° C. or over.

Moreover, in the case when $R^7$, $R^8$, $R^9$ and $R^{10}$ in general formula (3) are represented by —$NHR^{11}$ ($R^{11}$=a hydrogen atom), this compound is converted into a diazonium compound in an acid solvent by using sodium nitrite, potassium nitrite, nitrosyl sulfuric acid, isoamyl nitrite or the like so that a diazonium salt is obtained.

<<Synthesizing Method of a Compound Represented by General Formula (3)>>

The compound represented by the general formula (3) may be synthesized by using a compound represented by the following general formula (4):

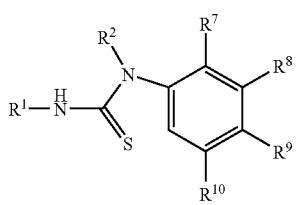

General formula (4)

In general formula (4), $R^1$ represents a hydrogen atom, an alkyl group or an aryl group. $R^2$ represents an alkyl group or an aryl group. Each of $R^7$, $R^8$, $R^9$ and $R^{10}$ independently represents a hydrogen atom or a monovalent substituent. Further, at least one of $R^7$, $R^8$, $R^9$ and $R^{10}$ represents —$NHR^{11}$. Here, $R^{11}$ represents a hydrogen atom or an acyl group.

In general formula (4), $R^1$, $R^2$, $R^7$, $R^8$, $R^9$, $R^{10}$ and $R^{11}$ represent the same as those described for $R^1$, $R^2$, $R^7$, $R^8$, $R^9$, $R^{10}$ and $R^{11}$ in general formula (3) respectively, with the preferable examples thereof being the same.

In the synthesizing method of the compound represented by general formula (3), the following conditions may be used.

The synthesizing reaction is an oxidizing reaction. As the oxidant, chlorine, bromine, iodine, sulfonyl chloride or sulfuryl chloride is preferably used, and from the viewpoint of handling and yield, bromine is most preferably used.

The amount of use of the oxidant is preferably in a range of 90% to 130% in the molar ratio with respect to the compound represented by general formula (4), and more preferably, it is in a range of 100% to 110%. When the amount of the oxidant is too small, the raw material tends to remain, while the amount of the oxidant is too great, side reaction products tend to increase.

As the solvent to be used in the reaction, any solvent may be used as long as it does not react with the oxidant, and acetic acid, propionic acid, acetonitrile, chloroform, methylene chloride, ethyl acetate or chlorobenzene is preferably used. In particular, from the viewpoint of the yield, acetic acid, chloroform and methylene chloride are preferably used. These solvents may be used as a mixed solvent. The amount of use of the solvent is set to such a degree as to dissolve the raw material; however, if the concentration is too high, the viscosity becomes too high to cause a reduction in the stirring efficiency, while, if the concentration is too low, the capacity efficiency is lowered. Therefore, it is preferably set in a range from 100% to 2000%, more preferably, 200% to 500%, with respect to the mass of the compound to be used, which is represented by general formula (4).

The reaction temperature is preferably selected from a range of −10° C. to 120° C. In general, the higher the temperature, the earlier the reaction is completed; however, since the present synthesizing method allows the reaction to quickly proceed even under room temperature, the reaction is preferably carried out in a range of −5° C. to 35° C. from the viewpoint of the yield. Moreover, in the case when acetic acid is used as the solvent, the reaction is preferably carried out at 10° C. or higher in order to prevent crystallization of the acetic acid.

The synthesizing process of the compound represented by general formula (3) can be carried out through a known method described in "Organic Functional Group Preparations Volume II" (written by Stanley R. Sandler, Wolf Karo (1971), published by Academic Press, Inc.), "Shin jikken kagaku kouza 14 Yuuki kagoubutsuno gouseito hannnouIII" (Synthesis and Reaction of Organic Compounds III, New Experimental Chemical Seminar 14) ((1976) published by Maruzen Co., Ltd.), pp. 2212–2220, J. Chem. Soc. (C) (1967) or the like.

The diazonium salt of the invention can be desirably used in a recording material which will be described later, and, in particular, it is preferably contained as a color-developing component in a heat sensitive recording layer of a heat sensitive recording material.

Moreover, the diazonium salt of the invention may be in an oil state or a crystal state, and from the viewpoint of handling, the diazonium salt in a crystal state at normal temperature is preferably used. These diazonium salts of the invention may be used alone, or two or more kinds thereof may be used in combination; alternatively, these may be used in combination with a known diazonium salt.

In the case when the diazonium salt of the invention is used in a heat sensitive recording layer of a recording material which will be described later, the content thereof is preferably set in a range of 0.02 to 5 g/m², more preferably, in a range of 0.1 to 4 g/m², from the viewpoint of the developed color density.

In order to stabilize the diazonium salt of the invention, a complex compound thereof is formed by using zinc chloride, cadmium chloride, tin chloride or the like; thus, it becomes possible to stabilize the diazonium salt.

The diazonium salt represented by general formula (1) reacts with a coupler, which being described later, to develop a color with a high color density. Also the diazonium salt is superior in the photo-decomposing property within a wavelength range of 380 to 460 nm of a fluorescent lamp or the like, and has a high-speed decomposing property capable of completing the fixing process even by light irradiation for a short period of time. Thus, it is very useful as a color-developing component to be used in a photo-fixing-type heat sensitive recording material.

<Coupler>

The following description will discuss a coupler (coupling component) that can be used in the recording material of the invention.

As the coupler, any compound may be applicable as long as it couples with the diazonium salt in a basic condition and/or a neutral condition to form a pigment. So-called four-equivalent couplers for a silver halide photographic photosensitive material are all applicable as the coupler. The couplers used in the invention can be appropriately selected among these couplers in accordance with desired hues.

Examples thereof include a so-called active methylene compound having a methylene group adjacent to a carbonyl group, phenol derivatives and naphthol derivatives, and the specific examples are listed in the following, and used within a range that satisfies the object of the invention.

Specific examples of the coupler include: resorcin, fluoroglucine, 2,3-dihydroxynaphthalene, sodium 2,3-dihydroxynaphthalene-6-sulfonate, 1-hydroxy-2-naphthoic acid morpholino propyl amide, sodium 2-hydroxy-3-naphthalene sulfonate, 2-hydroxy-3-naphthalene sulfonic acid anilide, 2-hydroxy-3-naphthalene sulfonic acid morpholino propyl amide, 2-hydroxy-3-naphthalene sulfonate-2-ethylhexyloxy propyl amide, 2-hydroxy-3-naphthalene sulfonate-2-ethylhexyl amide, 5-acetamide-1-naphthol, sodium 1-hydroxy-8-acetamide naphthalene-3,6-disulfonate, 1-hydroxy-8-acetamide naphthalene-3,6-disulfonic acid dianilide, 1,5-dihydroxy naphthalene, 2-hydroxy-3-naphthoic acid morpholino propyl amide, 2-hydroxy-3-naphthoic acid octyl amide, 2-hydroxy-3-naphthoic acid anilide, 5,5-dimethyl-1,3-cyclohexanedion, 1,3-cyclopentanedion, 5-(2-n-tetradecyloxy phenyl)-1,3-cyclohexanedion, 5-phenyl-4-methoxy carbonyl-1,3-cyclohexanedion, 5-(2,5-di-n-octyloxy phenyl)-1,3-cyclohexanedion, N,N'-dicyclohexyl barbituric acid, N,N'-di-n-dodecyl barbituric acid, N-n-octyl-N'-n-octadecyl barbituric acid, N-phenyl-N'-(2,5-di-n-octyloxy diphenyl) barbituric acid, N,N'-bis(octadecyloxycarbonylmethyl) barbituric acid, 1-phenyl-3-methyl-5-pyrazolone, 1-(2,4,6-trichlorophenyl)-3-anilino-5-pyrazolone, 1-(2,4,6-trichlorophenyl)-3-benzamide-5-pyrazolone, 6-hydroxy-4-methyl-3-cyano-1-(2-ethylhexyl)-2-pyridone, 2,4-bis(benzoyl acetamide) toluene, 1,3-bis-(pivaloyl acetamide methyl) benzene, benzoyl acetonitrile, thenoyl acetonitrile, acetoacetoanilide, benzoyl acetoanilide, pivaloyl acetoanilide, 2-chloro-5-(N-n-butyl sulfamoyl)-1-pivaloyl acetamide benzene, 1-(2-ethylhexyloxy propyl)-3-cyano-4-methyl-6-hydroxy-1,2-dihydropyridine-2-on, 1-(dodecyloxy propyl)-3-acetyl-4-methyl-6-hydroxy-1,2-dihydropyridine-2-on and 1-(4-n-octyloxy phenyl)-3-tert-butyl-5-amino pyrazole.

These couplers are disclosed in detail in JP-A Nos. 4-201483, 7-223367, 7-223368, 7-323660, 07-125446, 07-096671, 07-223367, 07-223368, 09-156229, 09-216468, 09-216469, 09-203472, 09-319025, 10-035113, 10-193801, and 10-264532.

Among the materials, compounds represented by the following general formula (2) or tautomers thereof are preferably used.

The following description will discuss the compounds represented by general formula (2) in detail.

$$E^1-CH_2-E^2 \qquad \text{General formula (2)}$$

In general formula (2), $E^1$ and $E^2$ independently represent electron-attractive groups respectively. Moreover, $E^1$ and $E^2$ may be bonded to each other to form a ring.

The electron-attractive groups represented by $E^1$ and $E^2$ refer to substituents having positive Hammett's $\sigma_p$ values, and these may be the same with or different from each other. Preferable examples thereof include: acyl groups, such as an acetyl group, a propionyl group, a pivaloyl group, a chloroacetyl group, a trichloroacetyl group, a trifluoroacetyl group, a 1-methyl cyclopropyl carbonyl group, a 1-ethylcyclopropyl carbonyl group, a 1-benzyl cyclopropyl carbonyl group, a benzoyl group, a 4-methoxybenzoyl group and a thenoyl group; oxycarbonyl groups, such as a methoxy carbonyl group, an ethoxy carbonyl group, a 2-methoxyethoxy carbonyl group and a 4-methoxyphenoxy carbonyl group; carbamoyl groups, such as a carbamoyl group, an N,N-dimethyl carbamoyl group, an N,N-diethyl carbamoyl group, an N-phenyl carbamoyl group, an N-[2,4-bis(octyloxy) phenyl] carbamoyl group, an N-[2,4-bis(octyloxy) phenyl] carbamoyl group and a morpholino carbonyl group; alkyl sulfonyl groups or aryl sulfonyl groups, such as a methane sulfonyl group, a benzene sulfonyl group and a toluene sulfonyl group; phosphono groups such as a diethyl phosphono group; heterocyclic groups such as a benzoxazole-2-yl group, a benzothiazole-2-yl group, a 3,4-dihydroquinazoline-4-on-2-yl group, a 3,4-dihydroquinazoline-4-sulfone-2-yl group; heterocyclic groups; nitro groups; imino groups; and cyano groups.

Moreover, the electron-attractive groups represented by $E^1$ and $E^2$ may be bonded to each other to form a ring. Regarding the rings formed by $E^1$ and $E^2$, a carbon ring or a hetero ring of 5 members or 6 members is preferable.

Representative compounds (B-1) to (B-38) serving as specific examples of the coupler represented by general formula (2) will be shown below; however, the invention is not intended to be limited by these. Additionally, tautomers of the couplers shown below are preferably used as well.

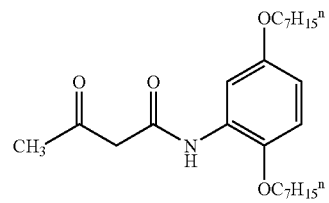
B-1

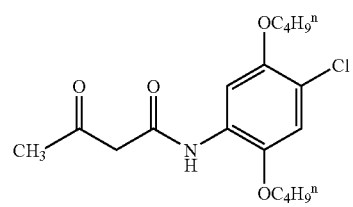
B-2

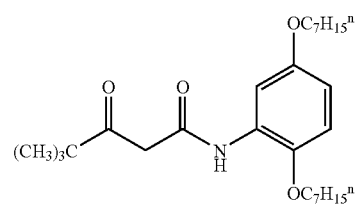
B-3

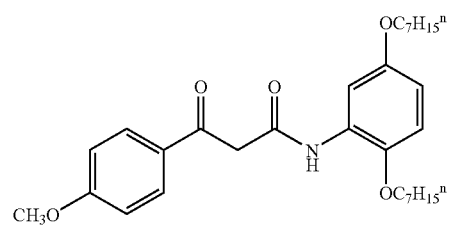
B-4

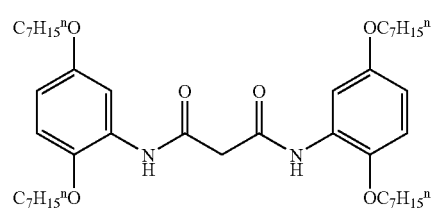
B-5

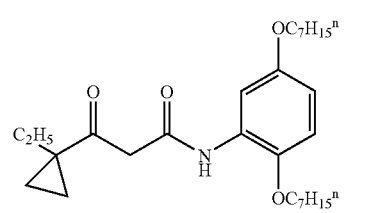
B-6

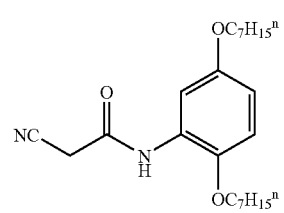
B-7

-continued
B-8
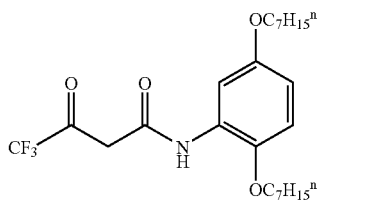
B-9
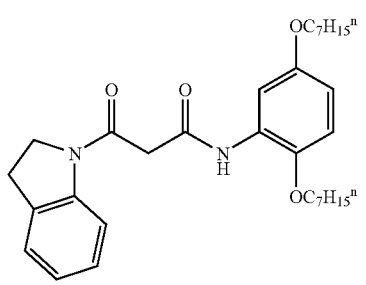
B-10
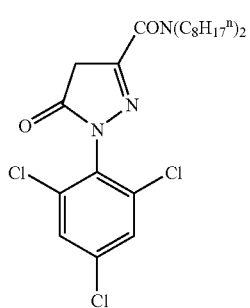
B-11
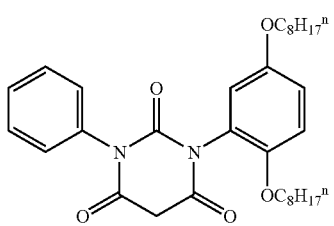
B-12
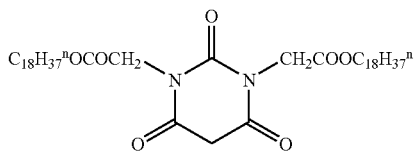
B-13
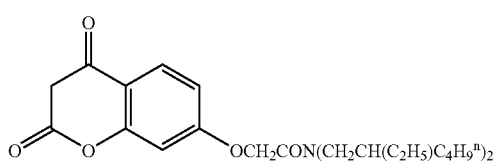
B-14
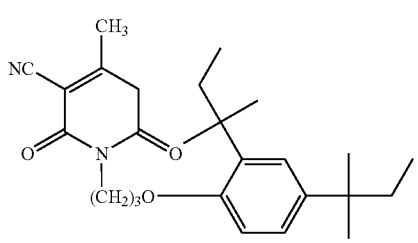
-continued
B-15
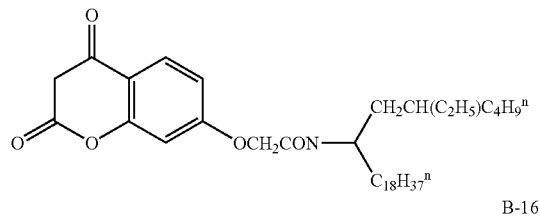
B-16
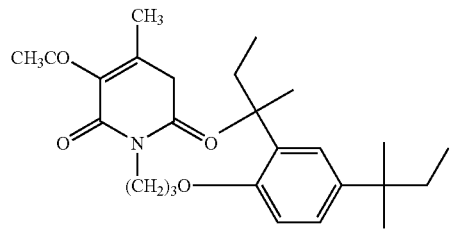
B-17
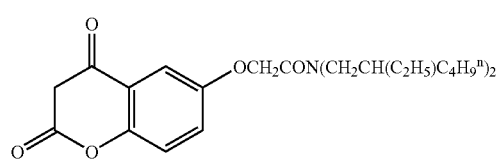
B-18
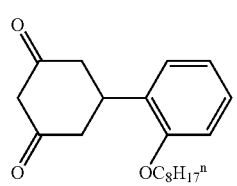
B-19
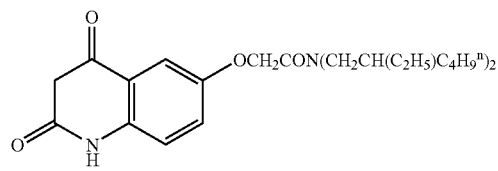
B-20
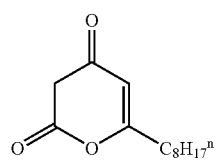
B-21
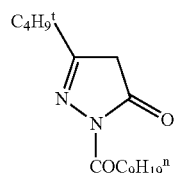
B-22
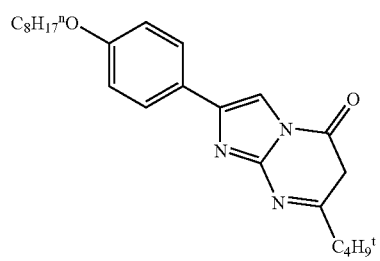

-continued
B-23
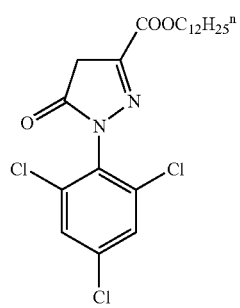
B-24
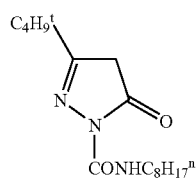
B-25
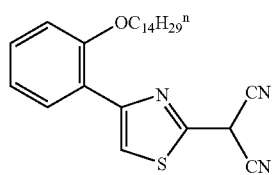
B-26
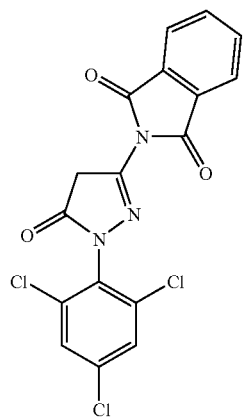
B-27
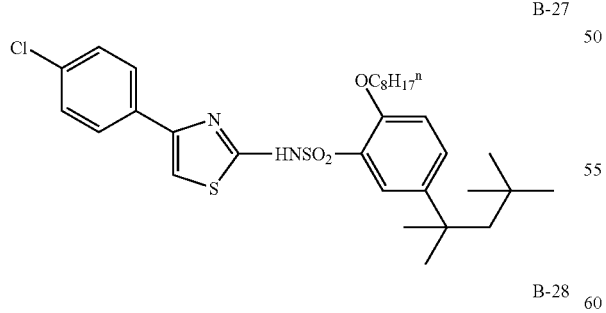
B-28
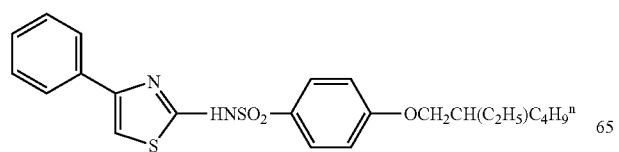
-continued
B-29
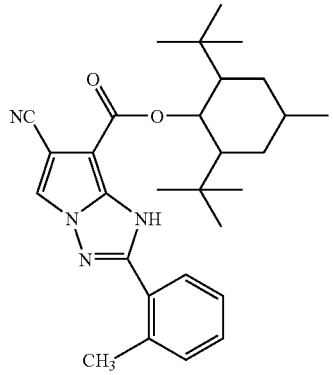
B-30
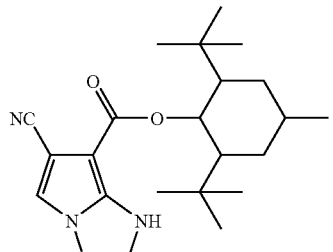
B-31
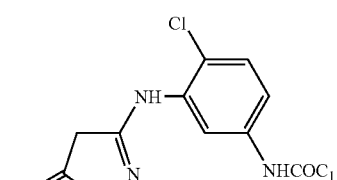
B-32
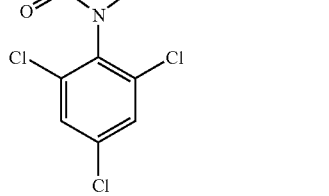

-continued

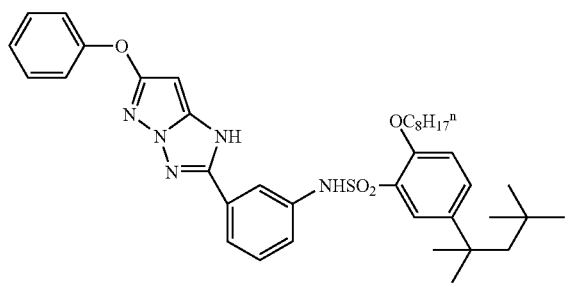
B-33

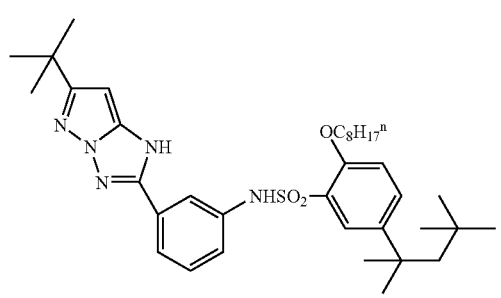
B-34

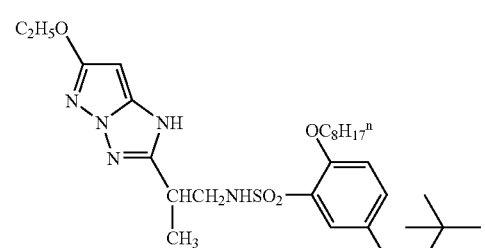
B-35

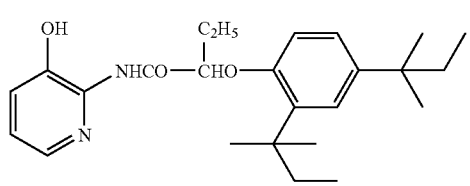
B-36

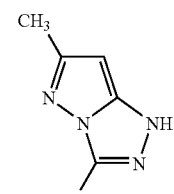
B-37

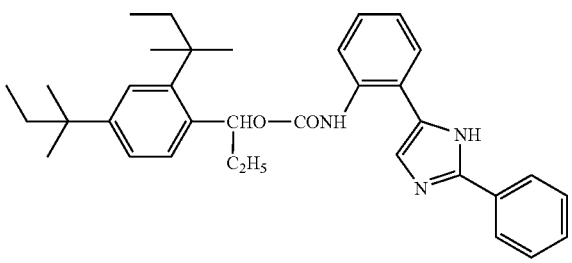
B-38

The tautomer of the coupler exists as an isomer of a coupler typically represented by the foregoing couplers. The coupler and the tautomer of the coupler are in the relation in which the coupler and the tautomer of the coupler structurally interconvert with ease, and as the coupler to be used in the invention, the tautomer is also desirably used.

<Forming Microcapsules>

In the recording material of the invention, the diazonium salt is preferably enclosed in microcapsules in order to improve the raw shelf life prior to the application. As the forming method of the microcapsules, an appropriate method is selected from known methods.

As the polymer substance for forming the capsule wall of the microcapsules, in particular, those substances having a glass transition temperature of 60 to 200° C. are preferably used considering that such polymer substance is required to have impermeability at room temperature and permeability when heated. Examples of such polymer substance include polyurethane, polyurea, polyamide, polyester, urea-formaldehyde resins, melamine resins, polystyrene, styrene-methacrylate copolymer, styrene-acrylate copolymer, and mixtures thereof.

Regarding the method for forming the microcapsules, in particular, an interfacial polymerizing method and an internal polymerizing method are preferably used. Specific examples of these and related reactants are described in, for example, specifications of U.S. Pat. Nos. 3,726,804 and 3,796,669. For example, in the case when polyurea or polyurethane is used as the capsule wall material, polyisocyanate and a second substance (for example, polyol, polyamine) that reacts with polyisocyanate to form the capsule wall are mixed in an aqueous medium or an oil medium to be capsulated, and the mixture is emulsified and dispersed in water, and then heated to cause polymerization on the interface of oil droplets so that microcapsule walls are formed. Here, even in the case when the addition of the second substance is omitted, it is possible to form polyurea.

In this invention, the polymer substance forming the microcapsule wall preferably comprises at least one kind of substance selected from polyurethane and polyurea.

Then, a method of manufacturing microcapsules containing diazonium salt compound (polyurea-polyurethane wall) will be discussed.

First, a diazonium salt compound is dissolved or dispersed in a hydrophobic solvent to prepare an oil phase that forms a core of a microcapsule. Moreover, at this time, polyvalent isocyanate is added as a wall material.

As a hydrophobic organic solvent that dissolves and disperses the diazonium salt, and is used for forming the core of microcapsules in the preparation of the oil phase, an organic solvent having a boiling point of 100 to 300° C. is preferably used, and examples thereof include: alkyl naphthalene, alkyl diphenyl ethane, alkyl diphenyl methane, alkyl biphenyl, alkyl terphenyl, chlorinated paraffin, phosphoric acid esters, maleic acid esters, adipic acid esters, phthalic acid esters, benzoic acid esters, carbonic acid esters, ethers, sulfuric acid esters and sulfonic acid esters, and two kinds or more thereof may be used in combination.

In the case when the diazonium salt to be encapsulated is poorly soluble in the organic solvent, a low-boiling-point solvent, to which the diazonium salt is highly soluble, may be used in combination as an assistant solvent. Examples of such low-boiling solvent include ethyl acetate, propyl acetate, isopropyl acetate, butyl acetate, methylene chloride, tetrahydrofran, acetonitrile and acetone.

For this reason, the diazonium salt compound preferably has an appropriate solubility to the high-boiling point hydrophobic solvent and the low-boiling-point solvent; more specifically, it preferably has a solubility of 5% to the solvent and a solubility of 1% or less to water.

Here, an aqueous solution in which water-soluble polymer has been dissolved is used as the water phase, and after the oil phase has been put into the aqueous solution, the mixture is emulsified and dispersed by using a homogenizer or the like. In this case, the water-soluble polymer enables the easy and uniform dispersion process, and also serves as a dispersing medium to stabilize the resultant aqueous solution obtained by the emulsion dispersion. In order to carry out the emulsion-dispersion process more evenly in a more stable manner, a surfactant may be added to at least one of the oil phase and the aqueous phase. Any known surfactant for emulsification may be used. Moreover, in the case when the surfactant is added, the amount of addition of the surfactant is preferably set to 0.1% to 5%, more preferably, 0.5 to 2%, with respect to the mass of the oil phase.

As the water-soluble polymer to be added to the aqueous polymer solution in which the prepared oil phase is dispersed, a water-soluble polymer having a solubility of 5% or more to water at a temperature of the emulsifying process, and specific examples thereof include: polyvinyl alcohol and modified compound thereof, polyacrylic acid amides and derivatives thereof, ethylene-vinyl acetate copolymer, styrene-maleic anhydride copolymer, ethylene-maleic anhydride copolymer, isobutylene-maleic anhydride copolymer, polyvinyl pyrrolidone, ethylene-acrylic acid copolymer, vinyl acetate-acrylic acid copolymer, carboxymethyl cellulose, methyl cellulose, casein, gelatin, starch derivatives, Arabic rubber and sodium alginic acid.

These water-soluble polymers preferably have no reactivity or low reactivity to an isocyanate compound, and in the case when those having a reactive amino group in a molecular chain such as gelatin, it is necessary to eliminate the reactivity thereof for example by preliminarily modifying it.

As the polyvalent isocyanate compound, a compound having a tri-functional or more isocyanate group is preferably used; however, di-functional isocyanate compound may be used. For example, dimers or trimers (biuret or isocyanurate), formed by using, as a main material, diisocyanate, such as xylene diisocyanate and hydrogenated materials thereof, hexamethylene diisocyanate, tolylenediisocyanate and hydrogenated materials thereof, and isophoronediisocyanate, may be used. Further, a polyfunctional material formed as an adduct between a polyol such as trimethylol propane and a di-functional isocyanate such as xylene diisocyanate, a compound formed by adding a high-molecular compound such as polyether having active hydrogen such as polyethylene oxide to an adduct between a polyol such as trimethylol propane and a di-functional isocyanate such as xylene diisocyanate, and a condensate of benzene isocyanate with formalin may be used.

Those compounds, described in JP-A Nos. 62-212190, 4-26189, 5-317694 and 10-114153, are preferably used.

The amount of use of the polyhydric isocyanate is so determined that the average particle size of the microcapsules becomes 0.3 to 12 μm with a wall thickness of 0.01 to 0.3 μm. Generally, the dispersion particle size is approximately 0.2 to 10 μm.

Thus, in the emulsifion-dispersion solution in which the oil phase is added to the water phase, the polymerizing reaction of polyvalent isocyanate takes place on the interface of the oil phase and the water phase, thereby forming polyurea walls.

Moreover, in the case when polyol and/or polyamine are preliminarily added to the water phase or the hydrophobic solvent of oil phase, the polyol and/or polyamine may react with polyvalent isocyanate to become one of the component constituting the microcapsule wall. In the reaction, it is preferable to maintain the reaction temperature at a high temperature or to add an appropriate polymerizing catalyst thereto, in order to accelerate the reaction speed.

Specific examples of these polyols or polyamines include: propylene glycol, glycerin, trimethylol propane, triethanol amine, sorbitol and hexamethylene diamine. In the case when polyol is added, polyurethane wall is formed.

With respect to the polyvalent isocyanate, polyol, reaction catalyst or polyamine and the like to form one portion of the wall agent, the detailed description thereof is found in known books (for example, Polyurethane Handbook, edited by Keiji Iwata, published by the Nikkan Kogyo Shinbun Ltd. (1987)).

The emulsifying process may be carried out by using a known emulsifier such as a homogenizer, manton gaulin, an ultrasonic disperser, a dissolver, Keddy mill. After the emulsifying process, the emulsified matter is heated to 30 to 70° C. so as to accelerate the capsule-wall-forming reaction. Moreover, during the reaction, it is necessary to add water thereto so as to reduce the collision possibility among capsules or to sufficiently carry out a stirring process, in order to prevent capsules from aggregating with each other.

Moreover, a material for preventing aggregation may be added to the solution and dispersed during the emulsification. As the polymerizing reaction progresses, a generation of $CO_2$ gas is observed and the completion of the generation of the gas is regarded as the termination of the capsule-wall forming reaction. Normally, the desired microcapsules containing diazonium salt is obtained by the reaction for several hours.

For example, the coupler to be used in the invention may be made in a state of solid dispersion by a sand mill or the like together with a water-soluble polymer, organic base and other color-developing assistant etc. More preferably, after the coupler has been dissolved in a high-boiling point organic solvent that is hardly soluble or insoluble to water, the resulting solution is mixed with a polymer aqueous solution (water phase) containing a surfactant and/or a water-soluble polymer as protective colloid, and emulsified by a homogenizer or the like so as to be used as an emulsified dispersion. In this case, if necessary, a low-boiling-point solvent may be used as a dissolving assistant. Moreover, the coupler and the organic base may be emulsion-dispersed independently, or may be mixed with each other, and then dissolved in a high-boiling point organic solvent so as to be emulsion-dispersed. Preferably, the size of the emulsion-dispersed particles is set to be 1 μm or less.

The amount of use of the coupler is preferably set to 0.1 to 30 parts by mass to 1 mass part of diazonium salt.

In this case, the high-boiling-point organic solvent to be used is appropriately selected, for example, from those high-boiling-point oils described in JP-A No. 2-141279. Among these, from the viewpoint of emulsion stability of the emulsion-dispersion, esters are preferably used, and tricresyl phosphate is more preferably used. The oils may be mixed with each other, or may be used in combination with other oil.

Moreover, a low-boiling-point assistant solvent may be further added to the organic solvent as a dissolution assistant, and as the assistant solvent, preferable examples include ethyl acetate, isopropyl acetate, butyl acetate and methylene chloride. Depending on cases, only the low-boiling-point assistant solvent without the high-boiling-point oil may be used.

Furthermore, the water-soluble polymer to be contained in the water phase as the protective colloid may be appropriately selected from known anionic polymers, nonionic polymers and amphoteric polymers; and among these, for example, polyvinyl alcohol, gelatin and cellulose derivatives may be preferably used.

As the surfactant to be contained in the water phase, any one of those anionic or nonionic surfactants that does not cause precipitation or aggregation by reacting with the protective colloid, may be appropriately selected, and used. As such surfactant, examples thereof include: alkyl benzene sulfonic acid soda, sodium alkyl sulfate, sodium dioctyl sulfosuccinate and polyalkylene glycol (such as polyoxy ethylene nonylphenyl ether).

In the recording material of the invention, it is also preferable to add an organic base as the basic substance in order to accelerate the coupling reaction between the diazonium salt and the coupler.

As the organic bases, examples thereof include nitrogen-containing compounds such as tertiary amines, piperidines, piperazines, amidines, formamidines, pyridines, guanidines and morpholines, and those compounds, described in JP-A Nos. 52-46806, 62-70082, 57-169745, 60-94381, 57-123086, 60-49991, Japanese Patent Application Publication (JP-B) Nos. 2-24916, 2-28479, 60-165288 and 57-185430, are preferably used. These materials may be used alone, or two or more kinds of these may be used in combination.

Among the materials, more specifically, preferable examples thereof include: piperazines, such as N,N'-bis(3-phenoxy-2-hydroxylpropyl) piperazine, N,N'-bis[3-(p-methylphenoxy)-2-hydroxypropyl] piperazine, N,N'-bis[3-(p-methoxyphenoxy)-2-hydroxypropyl] piperazine, N,N'-bis (3-phenylthio-2-hydroxypropyl) piperazine, N,N'-bis[3-(β-naphthoxy)-2-hydroxypropyl] piperazine, N-3-(β-naphthoxy)-2-hydroxypropyl-N'-methyl piperazine and 1,4-bis{[3-(N-methylpiperazino)-2-hydroxy] propyloxy) benzene; morpholines such as N-[3-(β-naphthoxy)-2-hydroxy] propylmorpholine, 1,4-bis(3-morpholino-2-hydroxypropyloxy) benzene and 1,8-bis(3-morpholino-2-hydroxypropyloxy) benzene; piperidines such as N-(3-phenoxy-2-hydroxypropyl) piperidine and N-dodecyl piperidine; guanidines such as triphenyl guanidine, tricyclohexyl guanidine and dicyclohexylphenyl guanidine.

With respect to the amount of use of the organic base, it is preferably set to 0.1 to 30 parts by mass per 1 mass part of diazonium salt.

With the amount of use of less than 0.1 parts by mass, a sufficient color-developing density is sometimes not obtained, and with the amount of use exceeding 30 parts by mass, the decomposition of the diazonium salt is sometimes accrelerated.

Moreover, in order to accelerate the color-developing reaction, that is, in order to completely carry out a thermal printing process rapidly with low energy, a color-developing assistant may be added to the heat sensitive recording layer in addition to the organic base. Here, the color-developing assistant is a substance that increases the color-developing density, or controls the color-developing temperature at the time of the thermal recording process, and is used for allowing the diazonium salt, the basic substance, the coupler or the like to easily react with each other, through its functions that lower the melting point of the coupler, the basic substance or the diazonium salt, or lower the softening point of capsule walls.

With respect to the color-developing assistant, examples thereof include: phenol derivatives, naphthol derivatives, alkoxy-substituted benzenes, alkoxy-substituted naphthalenes, aromatic ethers, thio ethers, esters, amides, ureides, urethane, sulfone amide compounds and hydroxyl compounds.

The color-developing assistant also includes a thermal fusing substance. The thermal fusing substance is a substance with a melting point of 50° C. to 150° C. which is in a solid state at normal temperature, is fused upon application of heat, and can dissolve the diazonium salt, the coupler, or the organic base or the like. More specifically, examples thereof include carboxylic acid amides, carboxylic acid amides substituted on N, ketone compounds, urea compounds, esters and the like.

In the heat sensitive recording material of the invention, in order to improve the fastness of a thermally-developed color image against light and heat or in order to reduce yellowing of unprinted portions (non-image portions) after the fixing process, known antioxidants or the like, such as those shown below, are also preferably used.

As the antioxidant, known antioxidants described in the following may be applied: for example, European Patent Applications Laid-Open Nos. 223739, 309401, 309402, 310551, 310552 and 459416, German Patent Application Laid-Open No. 3435443, JP-A Nos. 54-48535, 62-262047, 63-113536, 63-163351, 2-262654, 2-71262, 3-121449, 5-61166 and 5-119449, and U.S. Pat. Nos. 4,814,262 and 4,980,275. Moreover, various known additives that have been used in heat sensitive or pressure sensitive recording materials may also be used effectively.

As the various additives, examples thereof include those additives disclosed in the following patent gazettes: JP-A Nos. 60-107384, 60-107383, 60-125470, 60-125471, 60-125472, 60-287485, 60-287486, 60-287487, 60-287488, 61-160287, 61-185483, 61-211079, 62-146678, 62-146680, 62-146679, 62-282885, 63-051174, 63-89877, 63-88380, 63-088381, 63-203372, 63-224989, 63-251282, 63-267594, 63-182484, 1-239282, 4-291685, 4-291684, 5-188687, 5-188686, 5-110490, 5-170361, and JP-B Nos. 48-043294 and 48-033212.

Specific examples thereof include: 6-ethoxy-1-phenyl-2,2,4-trimethyl-1,2-dihydroquinoline, 6-ethoxy-1-octyl-2,2,4-trimethyl-1,2-dihydroquinoline, 6-ethoxy-1-phenyl-2,2,4-trimethyl-1,2,3,4-tetrahydroquinoline, 6-ethoxy-1-octyl-2,2,4-trimethyl-1,2,3,4-tetrahydroquinoline, nickel cyclohexanate, 2,2-bis(4-hydroxyphenyl) propane, 1,1-bis (4-hydroxyphenyl)-2-ethyl hexane, 2-methyl-4-methoxydiphenyl amine, 1-methyl-2-phenylindole and the like.

The amount of addition of the antioxidant or various additives is preferably in a range of 0.05 to 100 parts by mass per 1 mass part of diazonium salt, more preferably, 0.2 to 30 parts by mass.

The antioxidant and various additives may be contained in microcapsules together with the diazonium salt, may be contained in a form of a solid dispersion together with a coupler, basic substance and other color-developing assistants, may be contained in a form of a emulsion together with an appropriate emulsion assistant, or may be contained in both of the forms. Moreover, single kind of antioxidant or each of various additives may be used or plurality kinds of them may be used in combination. Furthermore, they may be contained in a protective layer.

The antioxidant and various additives are not necessarily required to be added to the same layer.

In the case when plurality kinds of the antioxidant and/or each of various additives are used in combination, they may be structurally classified, for example, to anilines, alkoxy benzenes, hindered phenols, hindered amines, hydroquinone derivatives, phosphor compounds and sulfur compounds may be classified in structures, and those having different structures may be used in combination, or a plurality of those having the same structure may be used in combination.

In order to reduce yellowing that occurs on the background portion after an image-recording process, a radical generating agent (compound that generates a radical upon application of light) for a photo-polymerizable composition or the like, may be added.

With respect to the radical generating agent, examples thereof include aromatic ketones, quinones, benzoin, benzoin ethers, azo compounds, organic disulfides and acyloxime esters.

The amount of addition of the radical generating agent is preferably in a range of 0.01 to 5 parts by mass per 1 mass part of the diazonium salt.

Similarly, in order to reduce yellowing, a polymerizable compound (hereinafter, referred to as "vinyl monomer") having an ethylenic unsaturated bond may be used. The vinyl monomer is a compound having at least one ethylenic unsaturated bond (vinyl group, vinylidene group, etc.) in its chemical structure, and has a chemical form such as a monomer or a prepolymer.

As the vinyl monomer, examples thereof include unsaturated carboxylic acids and salts thereof, esters between unsaturated carboxylic acids and aliphatic polyalcohols and amides between unsaturated carboxylic acids and aliphatic polyamine compounds. The vinyl monomer is used in an amount of 0.2 to 20 parts by mass per 1 mass part of the diazonium salt.

The radical generating agent and vinyl monomer may be used being contained in microcapsules together with the diazonium salt.

Moreover, an acid, such as citric acid, tartaric acid, oxalic acid, boric acid, phosphoric acid and pyrophosphoric acid, may be added as an acid stabilizer.

<Recording Material>

The recording material of the invention is characterized by containing the diazonium salt of the invention. The recording material is, for example, a heat sensitive recording material or a photosensitive recording material.

The following description will discuss the present invention in detail by exemplifying a case in which a heat sensitive recording material is used as the recording material of the invention. When the recording material of the invention is a heat sensitive material, the heat sensitive recording material is prepared by forming at least a heat sensitive recording layer on a support, the heat sensitive recording layer containing the diazonium salt represented by the general formula (1) and a coupler, and, if necessary, an organic base and other additives. Here, with respect to the diazonium salt represented by the general formula (1), plurality kinds of them may be used in combination.

The heat sensitive recording layer is formed by the following processes: a coating solution containing microcapsules including the diazonium salt represented by the general formula (1), a coupler and an organic base and other additives, if necessary, is prepared, and this coating solution is applied to a support such as paper and a synthetic resin film, and dried thereon.

The heat sensitive recording layer preferably contains an organic base.

The heat sensitive recording layer may be applied by employing a known coating method, such as a bar coating, a blade coating, an air knife coating, a gravure coating, a roll coating, a spray coating, a dip coating and a curtain coating.

Moreover, the dry amount of coat of the heat sensitive recording layer that has been applied and dried is preferably from 2.5 to 30 g/m$^2$.

The structure of the heat sensitive recording layer is not particularly limited, and, for example, the heat-sensitive recording layer may be a single layer comprising microcapsules, a coupler, an organic base, etc., or such components may be separately contained in each layer of a plurality of heat-sensitive recording layers. Moreover, a heat-sensitive recording layer may be provided by coating after an intermediate layer disclosed in JP-A No. 61-054980, etc. has been formed on a support.

As will be described later, a full-color developing, heat-sensitive, multi-recording layers may be used in which each recording layer corresponds to a respective mono-color having a different hue from others.

In the recording material of the invention, each of the heat sensitive recording layer, intermediate layer and protective layer which will be described later may contain a binder. As the binder, a known water-soluble polymer compound or a known latex may be appropriately selected, and used.

With respect to the water-soluble polymer compound, examples thereof include: methyl cellulose, carboxy methyl cellulose, hydroxyl ethyl cellulose, hydroxyl propyl cellulose, starch derivatives, casein, Arabic rubber, gelatin, ethylene-maleic anhydride copolymer, styrene-maleic anhydride copolymer, polyvinyl alcohol, silanol-modified polyvinyl alcohol, carboxy-modified polyvinyl alcohol, epichlorohydrin-modified polyamide, isobutylene-maleic anhydride salicylic acid copolymer, polyacrylic acid, polyacrylic acid amide, and modified substances thereof.

With respect to the latexes, examples thereof include styrene-butadiene rubber latex, methyl acrylate-butadiene rubber latex and vinyl acetate emulsion.

Among these, hydroxyl ethyl cellulose, starch derivatives, gelatin, polyvinyl alcohol derivatives, polyacrylic acid amide derivatives and the like are preferably used.

Moreover, the heat sensitive recording material may contain a pigment, and as the pigment, a known organic or inorganic material can be used; examples thereof include: kaolin, calcined kaolin, talc, agalmatolite, diatomaceous earth, calcium carbonate, aluminum hydroxide, magnesium hydroxide, zinc oxide, lithopone, amorphous silica, colloidal silica, calcined gypsum, silica, magnesium carbonate, titanium oxide, alumina, barium carbonate, barium sulfate, mica, microballoon, urea-formalin filler, polyester particles and cellulose filler.

Moreover, various known additives, such as a wax, an antistatic agent, an antifoamer, a conductive agent, a fluorescent dye, a surfactant, an ultraviolet-ray absorbing agent and the precursor thereof, may be used.

In the heat sensitive recording material, a protective layer may be formed on the heat sensitive recording layer, if necessary. Two or more protective layers may be laminated, if necessary.

As the material to be used in the protective layer, examples thereof include: water-soluble polymers, such as polyvinyl alcohol, carboxy-modified polyvinyl alcohol, vinyl acetate-acrylic amide copolymer, silicon-modified polyvinyl alcohol, starch, modified starch, methyl cellulose, carboxy methyl cellulose, hydroxyl methyl cellulose, gelatins, Arabic rubber, casein, hydrolysis products of styrene-maleic acid copolymer, half-ester hydrolysis products of styrene-maleic acid copolymer, hydrolysis products of isobutylene-maleic anhydride copolymer, polyacrylic amide derivatives, polyvinyl pyrrolidone, polystyrene sulfonic acid soda and alginic acid soda; and latexes such as styrene-butadiene rubber latex, acrylonitrile-butadiene rubber latex, methylacrylate-butadiene rubber latex and vinyl acetate emulsion.

The water-soluble polymer compound is subjected to a cross-linking process so that its shelf life stability is further improved. With respect to the cross-linking agent, a known cross-linking agent may be appropriately selected and used; and examples thereof include: water-soluble initial condensates such as N-methylol urea, N-methylol melamine and urea-formalin; dialdehyde compounds such as glyoxal and glutar aldehyde; inorganic cross-linking agents such as boric acid and borax; and polyamide epichlorohydrin.

The protective layer may further contain a known pigment, metal soap, wax and surfactant.

The amount of coat of the protective layer is preferably from 0.2 to 5 g/m$^2$, more preferably, from 0.5 to 2 g/m$^2$. The film thickness thereof is preferably from 0.5 to 2 µm, more preferably, from 0.5 to 2 µm.

Moreover, upon forming the protective layer, the protective layer may contain a known ultraviolet-ray absorbing agent or its precursor.

In the same manner as the formation of a heat sensitive recording layer on a support, the protective layer may be formed by the known coating method.

With respect to the support that is applicable to the heat sensitive recording material, any paper support for general pressure sensitive papers, heat sensitive papers, and dry or wet diazo copy paper may be used. Further, acidic paper, neutral paper, coated paper, plastic film laminated paper, synthetic paper, plastic films, such as polyethylene terephthalate and polyethylene naphthalate, and the like may be used.

In order to correct curling balance or to improve the chemical resistance of the rear face, a backcoat layer may be formed on the support. This backcoat layer is formed in the same manner as the protective layer.

Moreover, if necessary, an anti-halation layer may be formed between the support and the heat sensitive recording layer or on the surface of the side of the support bearing the heat sensitive recording layer, and a sliding layer, an antistatic layer, a sticker layer and the like may be formed on the rear surface of the support.

Furthermore, pieces of separate paper may be combined, mediated by adhesive layers, to form a labeled structure on the rear face of the support (on the surface of the side not bearing heat sensitive recording layer).

As described above, the application of the diazonium salt of the present invention to the heat sensitive recording layer makes it possible to obtain a high color-developing density, and to carry out a photo-fixing process at high speeds. Since this high photo-fixing speed achieves shortened recording time, and since the diazonium salt is superior in its own decomposing property, it is possible to achieve a sufficient fixing effect. Therefore, it becomes possible to prevent degradation in the degree of whiteness caused by colorimg of non-image portions (surface portions), and consequently to provide images that have high contrast, and are less susceptible to density variations. In other words, it is possible to achieve both of the improvements in stability and high speed as a recording material.

Moreover, by including the diazonium salt in the microcapsules, it becomes possible to further maintain the stability of the recording material for a long time.

<Image-forming Method>

An image-forming process using the heat sensitive recording material may be carried out by using the following method.

For example, the surface of the heat sensitive recording material on the side bearing the heat sensitive recording layer is heated image-wise by a heating device such as a thermal head so that in the heated portion of the heat sensitive recording layer, capsule walls containing polyurea and/or polyurethane are allowed to soften and become permeable to substances; thus, the coupler and the basic substance (organic base), located outside the capsules, are allowed to enter the microcapsules so that an image-wise color-developing process occurs to form an image. In this case, after the color-developing process, light having wavelengths corresponding to absorption wavelengths of the diazonium salt is further applied thereto (photo-fixing) so that the diazonium salt decomposes and loses its reactivity with the coupler, making it possible to fix the image. As mentioned above, the photo-fixing process allows unreacted diazonium salt to be decomposed to lose its reactivity; thus, it becomes possible to prevent density fluctuations in the resultant image and colored non-image portions (background portions) caused by generation of stains, that is, degradation in whiteness, and the subsequent degradation in image contrast.

With respect to the light source used in the photo-fixing, various lamps, such as fluorescent lamps, xenon lamps and mercury lamps, may be used, and the light-emitting spectrum of the light source preferably virtually coincides with the absorption spectrum of the diazonium salt in the heat sensitive recording material in view of the high fixing efficiency.

In particular, in the invention, the light source is preferably designed so that the center wavelength of light-emission to be applied is preferably from 380 to 460 nm.

Moreover, the heat sensitive recording material may be used as a thermal developing-type heat sensitive recording material on which an image-wise writing process is carried out by using light and the image is formed through a thermal developing process. In this case, the image-printing process is carried out by a light source such as a laser device in place of the heating device.

With respect to the heat sensitive recording material, a multi-color heat sensitive recording material may be formed by laminating a plurality of heat sensitive recording layers, each having a different developed-color hue. With respect to the heat sensitive recording layers to be laminated, for example, heat sensitive recording layers containing a photo-decomposable diazonium salt may be used.

The multi-color heat sensitive recording materials are described, for example, in the following patent gazettes: JP-A Nos. 3-288688, 4-135787, 4-144784, 4-144785, 4-194842, 4-247447, 4-247448, 4-340540, 4-340541, 5-34860, 5-194842 and 09-156229.

For example, the layer structure of a full-color heat sensitive recording material may be as the following. However, the invention is by no means limited by this example. Two diazonium salts having different photosensitive wavelength regions from each other is used. Each of the diazonium salts is combined with a coupler that can react with respective diazonium salts to develop colors of respective hue (different from each other). Combinations of each of the diazonium salts and the coupler are separately comprised in two heat-sensitive recording layers (B layer, C layer) that exhibit different developed-color hue from each other. And heat sensitive recording layer (A layer) comprises a combination of an electron-donating colorless dye and an electron-accepting compound. A full-color heat-sensitive recording material may include lamination of these layers (A layer, B layer, and C layer). Alternatively, a full-color heat sensitive recording material may be formed by laminating the two heat sensitive recording layers (B layer, C layer) and a heat sensitive recording layer (A layer) in which a diazonium salt having a photosensitive wavelength different from those of the layers (B layer and C layer) and a coupler capable of reacting with the diazonium salt to develop a color upon application of heat are combined.

More specifically, from the support side, a first heat sensitive recording layer (A layer), which contains an electron-donating colorless dye and an electron-accepting compound or a diazonium salt having the maximum absorption wavelength that is shorter than 350 nm and a coupler capable of reacting with the diazonium salt to develop a color upon application of heat, a second heat sensitive recording layer (B layer), which contains a diazonium salt having the maximum absorption wavelength that is 360 nm±20 nm and a coupler capable of reacting with the diazonium salt to develop a color upon application of heat, and a third heat sensitive recording layer (C layer), which contains a diazonium salt having the maximum absorption wavelength that is 400 nm±20 nm and a coupler capable of reacting with the diazonium salt to develop a color upon application of heat, may be successively laminated to form the material.

In this case, by selecting the developed-color hues of the respective heat sensitive recording layers so as to exhibit three subtractive primary colors, that is, yellow, magenta and cyan, it becomes possible to carry out a full-color image recording.

With respect to the layer structure of the full color recording material, any combination of the respective color developing layers of yellow, magenta and cyan may be used; and, from the viewpoint of color reproducibility, the layers are preferably laminated in the order of yellow, cyan and magenta or yellow, magenta and cyan from the support side.

With respect to the recording method in the case of the multi-color heat sensitive recording material, for example, the following processes may be carried out.

First, the third heat sensitive recording layer (C layer) is heated to allow the diazonium salt and coupler contained in the layer to develop a color. Next, by irradiating light having wavelengths of 400±20 nm on the recording material, unreacted diazonium salt contained in the C layer is decomposed. Next, sufficient heat is applied to the second heat sensitive recording layer (B layer) to allow the diazonium salt and coupler contained in the layer to develop a color. At this time, although the C layer is also strongly heated simultaneously, since the diazonium salt has already been decomposed to lose its color-developing capability, colors are not developed. Next, by irradiating light having wavelengths of 360±20 nm on the recording material, the diazonium salt contained in the B layer is decomposed. Last, sufficient heat is applied to the first heat sensitive recording layer (A layer) to allow the layer to develop a color. At this time, although the C layer and B layer are also strongly heated simultaneously, since the diazonium salts have already been decomposed to lose the color-developing capability, colors are not developed.

The recording material of the invention is preferably the multi-color heat sensitive recording material described above.

As described above, with respect to the color developing mechanism of the heat sensitive recording layer (A layer) that is directly laminated on the surface of the support, in addition to the combination of an electron-donating dye and an electron-accepting dye or the combination of diazonium salt and a coupler that is allowed to react with the diazonium salt upon application of heat, any one of a base color-developing system that develops a color upon contact with a basic compound, a chelate color-developing system and a color-developing system that reacts with a nucleophilic agent to cause a desorption reaction that develops a color, may be adopted. By forming a heat sensitive recording layer containing a diazonium salt and a coupler that reacts with the diazonium salt and develops a color on this heat sensitive recording layer, a multi-color heat sensitive recording material can be prepared.

In the case of a multi-color heat sensitive recording material, an intermediate layer may be placed between the respective heat sensitive recording layers in order to prevent color mixing between the mutual heat sensitive recording layers.

The intermediate layer is made of a water-soluble polymer compound such as gelatin, phthalized gelatin, polyvinyl alcohol and polyvinyl pyrrolidone, and may contain various additives depending on cases.

In the case when the recording material of the invention is a multi-color heat sensitive recording material having a photo-fixing type heat sensitive recording layer formed on a support, a light-transmittance adjusting layer or a protective layer is, or a light-transmittance adjusting layer and a protective layer are preferably formed further on the recording layers, if necessary.

The light-transmittance adjusting layer are disclosed in JP-A Nos. 9-39395, 9-39396, and 9-095487, etc.

In the case when a component that functions as a precursor of an ultraviolet-ray absorbing agent is used in the light-transmittance adjusting layer, since such component does not function as an ultraviolet-ray absorbing agent before irradiation of the light having a wavelength required for fixing and the layer has a high light-transmittance, upon fixing the photo-fixing type heat sensitive recording layer, it sufficiently transmits a light having wavelength within the range required for the fixing with a high transmittance in visible light rays, thereby causing no problems in the fixing of the photosensitive recording layer.

Here, after the light within the wavelength range required for the photo-fixing process (photo-decomposition of the diazonium salt by light irradiation) of the photo-fixing type heat sensitive recording layer has been applied, the precursor of the ultraviolet-ray absorbing agent reacts by the light and functions as an ultraviolet-ray absorbing agent. Most of the portions of light having wavelengths within the ultraviolet-ray range are absorbed by the ultraviolet-ray absorbing agent to cause a reduction in the transmittance so that it becomes possible to improve the light-fastness of the heat sensitive recording material. However, since the resultant ultraviolet-ray absorbing agent does not absorb the visible light, there is virtually no change in the transmittance for the visible light.

At least one light-transmittance adjusting layer may be provided in the heat sensitive recording material, and, in particular, it is preferably formed between the heat sensitive recording layer and the protective layer. Moreover, the protective layer may be designed to have functions of the light-transmittance adjusting layer, and commonly used as the adjusting layer.

EXAMPLES

The present invention will be further discussed by means of the following examples; however, the invention is by no means limited by these examples.

Example 1

Synthesis of Representative Compound A-1

134.3 g of compound 1-a represented by the following general formula was dissolved in 600 mL of methanol, 120 mL of concentrated hydrochloric acid was added to this mixture, and the resultant mixture was heated, and fluxed for 3 hours, and then cooled to 0° C. To this mixture, a solution of 22.9 g of sodium nitrite dissolved in 60 mL of water was dripped and the mixture was stirred at 10° C. for one hour. Then, 71.8 g of potassium hexafluorophosphate was further added to the reaction mixture and the mixture was stirred for 30 minutes at room temperature. 700 mL of water was added to this mixture so that crystal was deposited. The crystal thus deposited was filtered and collected, and after washed with water, the crystal was recrystallized using a mixed solvent of ethyl acetate and isopropanol. Thus, the obtained crystal was dried to obtain 149 g of representative compound A-1.

Compound 1-a

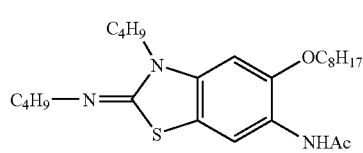

The resulting representative compound A-1 was identified by using a $^1$H-NMR. The obtained data is shown blow.

$^1$H-NMR (CDCl$_3$)δ; 7.97 (s, 1H), 6.48 (s, 1H), 4.37 (t, 2H), 4.06 (t, 2H), 3.24 (t, 2H), 1.91 (m, 2H), 1.60–1.69 (m, 4H), 1.28–1.48 (m, 14H), 0.85–1.00 (m, 9H).

The maximum absorption wavelength λmax within the ultraviolet and visible absorption spectrum in methanol was 413 nm, and the extinction coefficient ε was 2.0×10$^4$.

Example 2

Synthesis of Representative Compound A-3

23.7 g of compound 2-a represented by the following general formula was dissolved in 100 mL of methanol, 21 mL of concentrated hydrochloric acid was added to this mixture, and the mixture was heated, and fluxed for 3 hours, and then cooled to 0° C. To this mixture, a solution of 4.1 g of sodium nitrite dissolved in 10 mL of water was dripped and the mixture was stirred at 10° C. for 0.5 hour. Then, 12.9 g of potassium hexafluorophosphate was further added to the reaction mixture and the mixture was stirred for one hour at room temperature. 200 mL of water was added to this mixture so that crystal was deposited. The crystal thus deposited was filtered and collected, and after washed with water, the crystal was recrystallized using a mixed solvent of ethyl acetate and isopropanol. Thus, the crystal was dried to obtain 27.5 g of representative compound A-3.

Compound 2-a

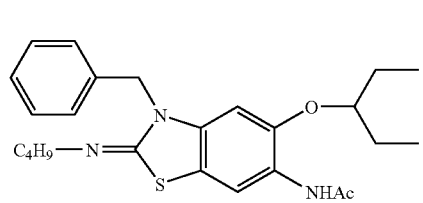

The resulting representative compound A-3 was identified by using a $^1$H-NMR. The obtained data is shown blow.

$^1$H-NMR (CDCl$_3$)δ; 8.01 (s, 1H), 7.24–7.40 (m, 5H), 6.32 (s, 1H), 5.34 (s, 2H), 4.37(m, 1H), 3.32 (t, 2H), 1.55–1.74 (m, 6H), 1.43 (m, 2H), 0.96 (t, 3H), 0.89 (t, 6H).

Here, the maximum absorption wavelength λmax within the ultraviolet and visible absorption spectrum in methanol was 412 nm, and the extinction coefficient ε was 1.5×10$^4$.

Example 3

Synthesis of Representative Compound A-4

10.3 g of compound 3-a represented by the following general formula was dissolved in 40 mL of methanol, 8 mL of concentrated hydrochloric acid was added to this mixture, and the mixture was heated, and fluxed for 2 hours, and then cooled to 0° C. To this mixture, a solution of 1.5 g of sodium nitrite dissolved in 4 mL of water was dripped and the mixture was stirred at 10° C. for 0.5 hour. Then, 4.8 g of potassium hexafluorophosphate was further added to the reaction mixture and the mixture was stirred for 1.5 hour at room temperature. 100 mL of water was added to this mixture so that crystal was deposited. The crystal thus deposited was filtered and collected, and after washed with water, the crystal was recrystallized using isopropanol. Thus, the crystal was dried to obtain 8.0 g of representative compound A-4.

Compound 3-a

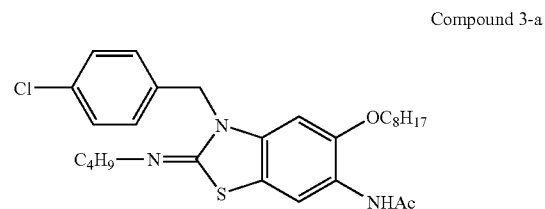

The resulting representative compound A-4 was identified by using a $^1$H-NMR. The obtained data is shown blow.

$^1$H-NMR (CDCl$_3$)δ; 7.99 (s, 1H), 7.33 (d, 2H), 7.21 (d, 2H), 6.43 (s, 1H), 5.30 (s, 2H), 4.24 (t, 2H), 3.29 (t, 2H), 1.80 (m, 2H), 1.67 (m, 2H), 1.20–1.43 (m, 12H), 0.86–0.97 (m, 6H).

The maximum absorption wavelength λmax within the ultraviolet and visible absorption spectrum in methanol was 412 nm, and the extinction coefficient ε was 1.7×10$^4$.

Example 4

Synthesis of Representative Compound A-5

9.8 g of compound 4-a represented by the following general formula was dissolved in 40 mL of methanol, 8 mL of concentrated hydrochloric acid was added to this mixture, and the mixture was heated, and fluxed for 2 hours, and then cooled to 0° C. To this mixture, a solution of 1.5 g of sodium nitrite dissolved in 4 mL of water was dripped and the mixture was stirred at 10° C. for 0.5 hour. Then, 4.8 g of potassium hexafluorophosphate was further added to the reaction mixture and the mixture was stirred for 1.5 hours at room temperature. 100 mL of water was added to this mixture so that crystal was deposited. The crystal thus deposited was filtered and collected, and after washed with water, the crystal was recrystallized using isopropanol. Thus, the crystal was dried to obtain 10.3 g of representative compound A-5.

Compound 4-a

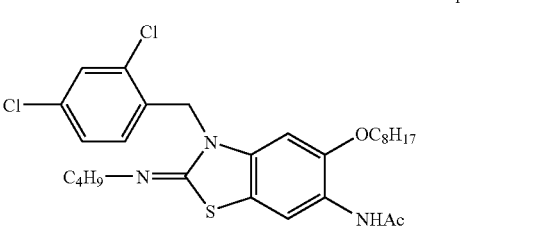

The resulting representative compound A-5 was identified by using a $^1$H-NMR. The obtained data is shown blow.

$^1$H-NMR (CDCl$_3$)δ; 8.10 (s, 1H), 7.46 (s, 1H), 7.26 (d, 1H), 7.11 (d, 1H), 6.40 (s, 1H), 5.36 (s, 2H), 4.22 (t, 2H), 3.29 (t, 2H), 1.82 (m, 2H), 1.64 (m, 2H), 1.20–1.43 (m, 12H), 0.86–0.98 (m, 6H).

Here, the maximum absorption wavelength λmax within the ultraviolet and visible absorption spectrum in methanol was 411 nm, and the extinction coefficient ε was $1.5 \times 10^4$.

Example 5

Synthesis of Representative Compound A-6

12.5 g of compound 5-a represented by the following general formula was dissolved in 50 mL of methanol, 9 mL of concentrated hydrochloric acid was added to this mixture, and the mixture was heated, and fluxed for 2.5 hours, and then cooled to 0° C. To this mixture, a solution of 1.8 g of sodium nitrite dissolved in 5 mL of water was dripped and the mixture was stirred at 10° C. for 0.5 hour. Then, 5.8 g of potassium hexafluorophosphate was further added to the reaction mixture and the mixture was stirred for 2 hours at room temperature. 100 mL of water was added to this mixture so that crystal was deposited. The crystal thus deposited was filtered and collected, and after washed with water, the crystal was recrystallized using a mixed solvent of ethyl acetate and isopropanol. Thus, the crystal was dried to obtain 8.8 g of representative compound A-6.

Compound 5-a

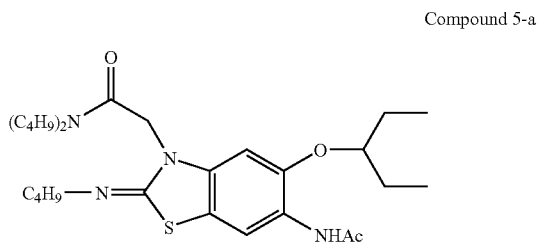

The resulting representative compound A-6 was identified by using a ¹H-NMR. The obtained data is shown blow.

¹H-NMR (CDCl₃)δ; 7.78 (s, 1H), 6.69 (s, 1H), 5.00 (s, 2H), 4.81 (m, 1H), 3.40 (t, 2H), 3.33 (t, 2H), 3.24 (t, 2H), 1.75–1.90 (m, 4H), 1.22–1.66 (m, 12H), 0.86–1.06 (m, 15H).

Here, the maximum absorption wavelength λmax within the ultraviolet and visible absorption spectrum in methanol was 411 nm, and the extinction coefficient ε was $1.3 \times 10^4$.

Example 6

Synthesis of Representative Compound A-9

7.8 g of compound 6-a represented by the following general formula was dissolved in 30 mL of methanol, 6 mL of concentrated hydrochloric acid was added to this mixture, and the mixture was heated, and fluxed for 2 hours, and then cooled to 0° C. To this mixture, a solution of 1.1 g of sodium nitrite dissolved in 3 mL of water was dripped and the mixture was stirred at 10° C. for 0.5 hour. Then, 3.6 g of potassium hexafluorophosphate was further added to the reaction mixture and the mixture was stirred for 2 hours at room temperature. 100 mL of water was added to this mixture so that crystal was deposited. The crystal thus deposited was filtered and collected, and after washed with water, the crystal was recrystallized using isopropanol. Thus, the crystal was dried to obtain 8.0 g of representative compound A-9.

Compound 6-a

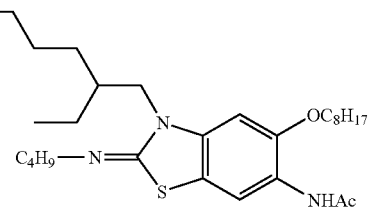

The resulting representative compound A-9 was identified by using a ¹H-NMR. The obtained data is shown blow.

¹H-NMR (CDCl₃)δ; 8.02 (s, 1H), 6.43 (s, 1H), 4.32 (s, 2H), 3.95 (d, 2H), 3.24 (t, 2H), 1.94 (m, 2H), 1.67 (m, 1H), 1.21–1.50 (m, 22H), 0.87–0.98 (m, 12H).

Here, the maximum absorption wavelength λmax within the ultraviolet and visible absorption spectrum in methanol was 414 nm, and the extinction coefficient ε was $1.7 \times 10^4$.

Example 7

Synthesis of Representative Compound A-13

7.0 g of compound 7-a represented by the following general formula was dissolved in 40 mL of methanol, 7.5 mL of concentrated hydrochloric acid was added to this mixture, and the mixture was heated, and fluxed for 3 hours, and then cooled to 0° C. To this mixture, a solution of 1.4 g of sodium nitrite dissolved in 4 mL of water was dripped and the mixture was stirred at 10° C. for 0.5 hour. Then, 4.4 g of potassium hexafluorophosphate was further added to the reaction mixture and the mixture was stirred for 2 hours at room temperature. 100 mL of water was added to this mixture so that crystal was deposited. The crystal thus deposited was filtered and collected, and washed with water. Thus, the crystal was dried to obtain 3.3 g of representative compound A-13.

Compound 7-a

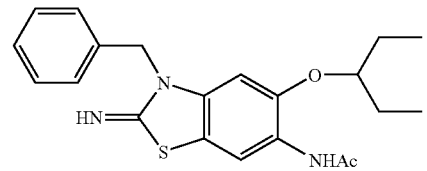

The resulting representative compound A-13 was identified by using a ¹H-NMR. The obtained data is shown blow.

¹H-NMR (dmso-d₆)δ; 8.60 (s, 1H), 7.32–7.41 (m, 5H), 7.24 (s, 1H), 5.49 (s, 2H), 4.89 (m, 1H), 3.98 (br, 1H), 1.64 (m, 4H), 0.85 (t, 6H).

Here, the maximum absorption wavelength λmax within the ultraviolet and visible absorption spectrum in methanol was 406 nm, and the extinction coefficient ε was $1.1 \times 10^4$.

Example 8

Synthesis of Representative Compound A-14

3.7 g of compound 8-a represented by the following general formula was dissolved in 15 mL of methanol, 2.7 mL of concentrated hydrochloric acid was added to this mixture, and the mixture was heated, and fluxed for 4 hours, and then cooled to 0° C. To this mixture, a solution of 0.5 g of sodium nitrite dissolved in 1.5 mL of water was dripped and the mixture was stirred at 10° C. for 0.5 hour. Then, 1.8 g of potassium hexafluorophosphate was further added to the reaction mixture and the mixture was stirred for one hour at room temperature. 50 mL of water was added to this mixture so that crystal was deposited. The crystal thus deposited was filtered and collected, and after washed with water, the crystal was recrystallized using isopropanol. Thus, the crystal was dried to obtain 4.5 g of representative compound A-14.

Compound 8-a

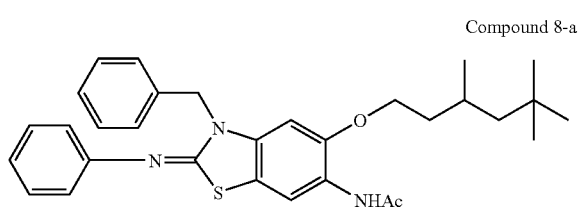

The resulting representative compound A-14 was identified by using a $^1$H-NMR. The obtained data is shown blow.

$^1$H-NMR (CDCl$_3$)δ; 8.09 (s, 1H), 6.90–7.52 (m, 10H), 6.51 (s, 1H), 5.48 (s, 2H), 4.21 (t, 2H), 1.83 (m, 1H), 1.64 (m, 2H), 1.15 (t, 2H), 0.96 (d, 3H), 0.89 (s, 9H).

Here, the maximum absorption wavelength λmax within the ultraviolet and visible absorption spectrum in methanol was 418 nm, and the extinction coefficient ε was 2.6×10$^4$.

Example 9

Synthesis of Representative Compound A-16

8.8 g of compound 9-a represented by the following general formula was dissolved in 30 mL of methanol, 6 mL of concentrated hydrochloric acid was added to this mixture, and the mixture was heated, and fluxed for 2 hours, and then cooled to 0° C. To this mixture, a solution of 1.2 g of sodium nitrite dissolved in 3 mL of water was dripped and the mixture was stirred at 10° C. for 0.5 hour. Then, 3.8 g of potassium hexafluorophosphate was further added to the reaction mixture and the mixture was stirred for 2 hours at room temperature. 100 mL of water was added to this mixture so that crystal was deposited. The crystal thus deposited was filtered and collected, and after washed with water, the crystal was recrystallized using a mixed solvent of ethyl acetate and isopropanol. Thus, the crystal was dried to obtain 7.5 g of representative compound A-16.

Compound 9-a

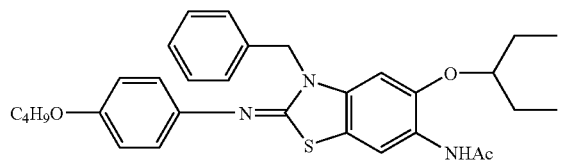

The resulting representative compound A-16 was identified by using a $^1$H-NMR. The resulting data was shown blow.

$^1$H-NMR (CDCl$_3$)δ; 8.02 (s, 1H), 7.30–7.43 (m, 5H), 7.02 (d, 2H), 6.92 (d, 2H), 6.38 (s, 1H), 5.48 (s, 2H), 4.37 (m, 1H), 3.98 (t, 2H), 1.78 (m, 2H), 1.64 (m, 4H), 1.53 (m, 2H), 0.99 (t, 3H), 0.88 (t, 6H).

Here, the maximum absorption wavelength λmax within the ultraviolet and visible absorption spectrum in methanol was 425 nm, and the extinction coefficient ε was 1.1×10$^4$.

Example 10

A heat sensitive recording material was prepared as the recording material of the invention in the following processes.

(Preparation of a Phthalized Gelatin Solution)

Phthalized gelatin (brand name; MGP gelatin, made by Nippi Collagen Co., Ltd.) (32 parts by mass), 1,2-benzothiazoline-3-on (3.5% methanol solution, made by Daito Chemical Industries, Ltd.) (0.9143 parts by mass) and ion exchange water (367.1 parts by mass) were mixed, and dissolved at 40° C. so that a phthalized gelatin aqueous solution was prepared.

(Preparation of Alkali-treated Gelatin Solution)

Alkali-treated low-ionic gelatin (brand name; #750 gelatin, made by Nitta Gelatin Inc.) (25.5 parts by mass), 1,2-benzothiazoline-3-on (3.5% methanol solution, made by Daito Chemical Industries, Ltd.) (0.7286 parts by mass), calcium hydroxide (0.153 parts by mass) and ion exchange water (143.6 parts by mass) were mixed, and dissolved at 50° C. so that an alkali-treated gelatin aqueous solution was prepared.

(Preparation of Diazonium Salt Compound-containing Microcapsule Solution A)

4.7 g of a diazonium compound (representative compound A-1), 9.6 g of tricresyl phosphate and 0.4 g of diphenyl (2,4,6-trimethyl benzoyl) phosphine oxide (brand name: Lucirin TPO, BASF Japan Ltd.) were added in 16.1 g of ethyl acetate and evenly mixed. Next, 8.6 g of a mixture of xylylene diisocyanate/trimethyl propane adduct and xylylene diisocyanate/bisphenol A adduct (brand name; Takenate D119N (50% ethyl acetate solution), made by Takeda Chemical Industries, Ltd.) as a capsule wall material was added to this mixture, and evenly dispersed to obtain solution I.

Next, solution I was added to a mixture of 56.5 g of the phthalized gelatin aqueous solution, 16.5 g of ion exchange water and 0.35 g of Scraph AG-8 (50% by mass; made by Nippon Fine Chemical Co., Ltd.), and emulsified and dispersed at 40° C. at 10000 rpm by using a homogenizer. 20 g of water was added to the resultant emulsion, and evenly dispersed. And then, the emulsion was subjected to an encapsulating reaction at 40° C. for 3 hours while being stirred. Thereafter, 8.2 g of Amberlite IRC50 (made by Organo Corporation) was added to the emulsion, and the emulsion was further stirred for one hour. Next, the ion exchange resin was filtered and removed so that the solids content of the capsule solution was adjusted to 20.0%; thus, a diazonium salt-containing microcapsule solution A was obtained. The particle size of the resultant microcapsules was measured (by a LA-700, made by Horiba Ltd.) and found to be 0.57 μm in median diameter.

(Preparation of Coupler Emulsion Solution B)

9.9 g of a coupler (representative compound B-1), 9.9 g of triphenyl guanidine (made by Hodogaya Chemical Co., Ltd.), 20.8 g of 4,4'-(m-phenylene diisopropylidene) diphenol (brand name; bisphenol M (made by Mitsui Petrochemical Industries, Ltd.), 3.3 g of 3,3,3',3'-tetramethyl-5,5',6,6'-tetra (1-propyloxy)-1,1'-spirobisindane (made by Sankyo Chemical Industries, Ltd.), 13.6 g of 4-(2-ethyl-1-hexyloxy) benzene sulfonic acid amid (made by Manac Incorporated), 6.8 g of 4-n-pentyloxy benzene sulfonic acid amid (made by Manac Incorporated), and 4.3 g of calcium dodecylbenzene sulfonate (brand name: Pionin A-41-C, 70% methanol solution; made by Takemoto Oil & Fat Co., Ltd.) were added in 33.0 g of ethyl acetate and dissolved to obtain solution II.

Separately, 107.5 g of ion exchange water was added to 206.3 g of an alkali-treated gelatin solution, solution II was added to the resultant gelatin solution, and the resultant mixture was emulsified and dispersed at 40° C. at 10000 rpm for 10 minutes by using a homogenizer. The resulting emulsion was depressurized and heated, and after ethyl acetate had been removed therefrom, the concentration was adjusted to set the solids content at 26.5% by mass. The particle diameter of the resultant coupler emulsion measured (by a LA-700, made by Horiba Ltd.) and found to be 0.21 µm in median diameter. 9 g of SBR latex (brand name: SN-307, 48% by mass solution, made by Sumika ABS Latex (K.K.)) the concentration of which was adjusted to 26.5% by mass was added to the emulsion to obtain a coupler emulsion B.

(Preparation of Heat Sensitive Recording Layer Coating Solution C)

Diazonium-salt-containing microcapsule solution A and coupler emulsion B was mixed so as to be set a mass ratio of coupler/diazonium salt compound to 2.2/1 to obtain a heat sensitive recording layer coating solution C.

(Preparation of Light-transmittance Adjusting Layer Coating Solution)

1. Preparation of Ultraviolet-ray-absorbing Agent Precursor Microcapsule Solution 14.5 parts by mass of [2-allyl-6-(2H-benzotriazole-2-yl)-4-t-octylphenyl] benzene sulfonate serving as an ultraviolet-ray absorbing agent precursor, 5.0 parts by mass of 2,2'-t-octylhydroquinone, 1.9 parts by mass of tricresyl phosphate, 5.7 parts by mass of α-methylstyrene dimmer (brand name: MSD-100, made by Mitsui Chemicals Inc.), 0.45 parts by mass of calcium dodecylbenzene sulfonate (brand name: Pionin A-41-C (70% methanol solution), made by Takemoto Oil & Fat Co., Ltd.) were added to 71 parts by mass of ethyl acetate and dissolved evenly. 54.7 parts by mass of xylylene diisocyanate/trimethylol propane adduct (brand name; Takenate D110N (75% ethyl acetate solution), made by Takeda Chemical Industries, Ltd.) as a capsule wall material was added to the mixture and the mixture was evenly dispersed to obtain an ultraviolet-ray-absorbing agent precursor mixture.

Separately, to 52 parts by mass of itaconic acid-modified polyvinyl alcohol (brand name: KL-318, made by Kuraray Co., Ltd.) were added 8.9 parts by mass of a 30% by mass phosphoric acid solution and 532.6 parts by mass of ion exchange water to prepare a PVA aqueous solution to be used for an ultraviolet-ray-absorbing agent precursor microcapsule solution.

The ultraviolet-ray-absorbing agent precursor mixture was added to 516.06 parts by mass of the PVA aqueous solution to be used for an ultraviolet-ray-absorbing agent precursor microcapsule solution and emulsified and dispersed at 20° C. by using a homogenizer (made by Nihon Seiki Seisakusho (K.K.)). 254.1 parts by mass of ion exchange water was added to the resultant emulsion and after having been evenly mixed, the emulsion was subjected to a capsulating reaction for 3 hours while being stirred at 40° C. Thereafter, 94.3 parts by mass of ion-exchange resin Amberlite MB-3 (made by Organo Corporation) was added to the emulsion and the emulsion was further stirred for one hour. Thereafter, the ion exchange resin was filtered and removed so that the concentration was adjusted to set the solids content at 13.5%. The particle diameter of the resultant microcapsules was measured (by a LA-700, made by Horiba Ltd.) and found to be 0.23±0.05 µm in median diameter. 2.416 parts by mass of carboxy-modified styrene-butadiene latex (brand name: SN-307, (48% by mass aqueous solution), made by Sumitomo Naugatuck Co., Ltd.) and 39.5 parts by mass of ion exchange water were added and mixed to 859.1 parts by mass of this capsule solution to prepare an ultraviolet-ray absorbing-agent precursor microcapsule solution.

2. Preparation of Light-transmittance Adjusting Layer Coating Solution 1000 parts by mass of the ultraviolet-ray absorbing-agent precursor microcapsule solution, 5.2 parts by mass of a fluorine-based surfactant [brand name: MEGAFACE F-120, made by Dainippon Ink and Chemicals, Incorporated) (5% by mass aqueous solution)], 7.75 parts by mass of 4% by mass sodium hydroxide solution and 73.39 parts by mass of (4-nonylphenoxy trioxyethylene) sodium butylsulfonate (made by Sankyo Chemical Industries, Ltd., 2.0% by mass aqueous solution) were mixed to obtain a light-transmittance adjusting layer coating solution.

(Preparation of Protective Layer Coating Solution)

1. Preparation of Polyvinyl Alcohol Solution for Protective Layer 160 parts by mass of vinyl alcohol-alkyl vinyl ether copolymer (brand name: EP-130, made by Denki Kagaku Kogyo Kabushiki Kaisha), 8.74 parts by mass of a mixed solution of sodium alkyl sulfonate and polyoxyethylene alkyl ether phosphate (brand name: Neoscore CM-57, (54% aqueous solution), made by Toho Chemical Industry Co., Ltd.) and 3832 parts by mass of ion exchange water were mixed, and dissolved at 90° C. for one hour to obtain an even polyvinyl alcohol solution for protective layer.

2. Preparation of Pigment Dispersion for Protective Layer 0.2 parts by mass of an anionic special polycarboxylic acid type polymer activator (brand name: Poise 532A (40% by mass aqueous solution), made by Kao Corporation) and 11.8 parts by mass of ion exchange water were added to 8 parts by mass of barium sulfate (brand name: BF-21F with a barium sulfate content of 93% or more, made by Sakai Chemical Industry Co., Ltd.) and dispersed by using a DYNO-Mill. The particle diameter of this dispersion was measured (by an LA-910, made by Horiba Ltd.), and found to be 0.15 µm or less in median diameter.

To 45.6 parts by mass of the dispersion, 8.1 parts by mass of colloidal silica (brand name: SNOWTEX O (20% by mass aqueous solution), made by Nissan Chemical Industries, Ltd.) was added to obtain a desired pigment dispersion for protective layer.

3. Preparation of Matting-agent Dispersion for Protective Layer 3.81 parts by mass of a water dispersion of 1,2-benzisothiazoline-3-on (brand name: PROXEL made by B.D.I.C.I (K.K.)) and 1976.19 parts by mass of ion exchange water To 220 parts by mass of wheat starch (brand name: Wheat Starch S, made by Nisshin Shokuryo Kogyo (K.K.))

were added and mixed, and evenly dispersed to obtain a matting agent dispersion for protective layer.

4. Preparation of Coating Blend Solution for Protective Layer 40 parts by mass of the compound (K) (brand name: MEGAFACE F-120, made by Dainippon Ink and Chemicals, Incorporated) (5% by mass aqueous solution), 50 parts by mass of (4-nonylphenoxy trioxyethylene) sodium butylsulfonate (2.0% by mass aqueous solution, made by Sankyo Chemical Industries, Ltd.), 49.87 parts by mass of the pigment dispersion for protective layer, 16.65 parts by mass of the matting agent dispersion for protective layer and 48.7 parts by mass of zinc stearate dispersion solution (brand name: Hydrin F115, 20.5% by mass aqueous solution, made by Chukyo Oil & Fat Co., Ltd.) were added to 1000 parts by mass of the polyvinyl alcohol solution for protective layer and evenly mixed to obtain a coating blend solution for protective layer.

(Formation of Support with an Undercoat Layer)

1. Preparation of an Undercoat Layer Coating Solution 40 parts by mass of enzymatically decomposed gelatin (average molecular weight: 10000, viscosity in PAGI method: 1.5 mPa.s (15 mP), gelling strength in PAGI method: 20 g) was added to 60 parts by mass of ion exchange water, stirred and dissolved at 40° C. to prepare a gelatin solution for undercoat layer.

Separately, 8 parts by mass of water-swelling synthetic mica (aspect ratio: 1000, brand name: Somashif ME100, made by Co-op Chemical Co., Ltd.) and 92 parts by mass of water were mixed, and the mixture was then dispersed in a wet manner by using a viscomill to obtain a mica dispersion having an average particle size of 2.0 μm. Water was added to this mica dispersion so as to set the mica concentration to 5% by mass, and the dispersion was mixed evenly to prepare a desired mica dispersion solution.

Thereafter, 120 parts by mass of water and 556 parts by mass of methanol were added to 100 parts by mass of 40% by mass solution of the undercoat layer coating solution at 40° C., and after having been sufficiently stirred and mixed, 208 parts by mass of 5% by mass solution of the mica dispersion was added to the mixture, and the mixture was sufficiently stirred and mixed, and 9.8 parts by mass of 1.66% by mass polyethylene oxide-based surfactant was added to the mixture. Then, with the solution temperature being maintained at 35° C. to 40° C., 7.3 parts by mass of a gelatin hardening agent of epoxy compound was added thereto to prepare an undercoat layer coating solution (5.7% by mass).

2. Formation of a Support with an Undercoat Layer

Wood pulp composed of 50 parts by mass of LBPS and 50 parts by mass of LBPK was beaten by a double disc refiner to 300 ml in Canadian freeness, and 0.5 part by mass of epoxidized behenic acid amide, 1.0 mass part of anionic polyacrylic amide, 1.0 mass part of aluminum sulfate, 0.1 part by mass of polyamidepolyamine epichlorohydrin and 0.5 part by mass of cationic polyacrylic amide were added to the beaten pulp, each amount (part) representing absolute dry weight ratio with respect to pulp, so that base paper was formed with a basis weight of 114 g/m$^2$ by using a Fourdrinier machine, and then the thickness of the base paper was adjusted to 100 μm by calendering the base paper.

Next, after both the surfaces of the base paper had been subjected to corona discharging processes, one surface was coated with polyethylene by using a melt extruder so that a resin layer having a mat face having the thickness of 36 μm was formed (this face was referred to as "rear face"). Next, the face opposite to the face coated with the resin layer was coated with polyethylene containing 10% by mass of anatase-type titanium dioxide and a slight amount of ultramarine blue pigment by using a melt extruder so that a resin layer made of a gloss face having the thickness of 50 μm was formed (this face was referred to as "front face"). After the polyethylene-resin coated face of the rear face had been subjected to a corona discharging process, a mixture of aluminum oxide (brand name; alumina sol 100, made by Nissan Chemical Industries, Ltd.)/silicon dioxide (brand name; SNOWTEX O, made by Nissan Chemical Industries, Ltd.)=1/2 (mass ratio) was dispersed in water, and applied thereto as an antistatic agent, in an amount of 0.2 g/m$^2$ as a dry weight. Next, after the polyethylene resin coated face on the front face had been subjected to a corona discharging process, the undercoat layer coating solution was applied thereto so that the amount of mica coated became 0.26 g/m$^2$; thus, a support with an undercoat layer was obtained.

(Coating Processes)

On the surface of the support with the under-coat layer, the following three layers were successively applied and formed simultaneously in succession from the bottom: the heat sensitive recording layer coating solution C, the light-transmittance adjusting layer coating solution and the protective layer coating solution. And these layers were successively dried under conditions at 30° C., 30% r.h. and at 40° C., 30% r.h.; thus, a desired heat sensitive recording material was obtained.

Example 11

The same processes as those of example 10 were carried out except that in place of representative compound (A-1), representative compound (A-3) was used as the diazonium salt to form a heat sensitive recording material of example 11.

Example 12

The same processes as those of example 10 were carried out except that in place of representative compound (A-1), representative compound (A-4) was used as the diazonium salt to form a heat sensitive recording material of example 12.

Example 13

The same processes as those of example 10 were carried out except that in place of representative compound (A-1), representative compound (A-5) was used as the diazonium salt to form a heat sensitive recording material of example 13

Example 14

The same processes as those of example 10 were carried out except that in place of representative compound (A-1), representative compound (A-6) was used as the diazonium salt to form a heat sensitive recording material of example 14.

Example 15

The same processes as those of example 10 were carried out except that in place of representative compound (A-1), representative compound (A-9) was used as the diazonium salt to form a heat sensitive recording material of example 15.

Example 16

The same processes as those of example 10 were carried out except that in place of representative compound (A-1), representative compound (A-16) was used as the diazonium salt to form a heat sensitive recording material of example 16.

Comparative Example 1

The same processes as those of example 10 were carried out except that in place of representative compound (A-1), the following comparative compound 1 was used as the diazonium salt to form a heat sensitive recording material of comparative example 1.

Comparative compound 1

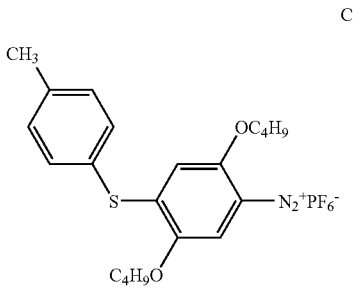

[Evaluation]

(Color-developing Test)

A thermal head made by Kyocera Corporation (KST type) was used with its applied power and pulse width with respect to the thermal head being determined so as to set a recording energy per unit area to 23 mJ/mm² so that a thermal printing process was carried out on each of the heat sensitive recording materials to obtain an image. Next, each of the heat sensitive recording materials was exposed with an ultraviolet-ray lamp having a light-emission center wavelength of 450 nm and an output of 40 W for 10 seconds. The resultant color-developing density and background density were measured.

(Shelf Stability Test)

The respective heat sensitive recording materials prior to recording were forcefully stored for 72 hours under the conditions of 60° C. and 30% r.h. Thereafter, the same thermal recording and density measuring processes were carried out in the same manner as described above.

(Photo-fixing Property Test)

The respective unprinted heat sensitive recording materials were exposed to an ultraviolet-ray lamp having a light-emitting center wavelength of 450 nm and an output of 40 W with varying exposed time, and they were then subjected to the same thermal recording and density measuring processes as described above. The color-developing density was plotted against the fixing time, and the ratio of the gradient of each plot to the following gradient of the comparative compound was calculated. Here, the greater the figure, the more superior the fixing property.

(Background Light-fastness Test)

An Atlas C. I 65 weather meter was used to irradiate the background portion with xenon light (85000 lux) for four days, and the background density after the xenon irradiation was measured.

(Density Measurements)

In each of the tests, the densities of the color-developing portion and fogging were measured as the density at Y position by using a Macbeth RD 918. The density of the surface portion was measured as the density at Y position.

Table 1 shows the results of the tests.

TABLE 1

| | Color-developing test | | Shelf stability test Color-developing density | Photo-fixing property test Fixing sensitivity | Background light-fastness test Background density |
|---|---|---|---|---|---|
| | Color-developing density | Background density | | | |
| Example 10 | 1.52 | 0.08 | 1.48 | 1.45 | 0.08 |
| Example 11 | 1.53 | 0.08 | 1.49 | 1.44 | 0.08 |
| Example 12 | 1.51 | 0.09 | 1.46 | 1.43 | 0.09 |
| Example 13 | 1.50 | 0.09 | 1.45 | 1.43 | 0.09 |
| Example 14 | 1.50 | 0.10 | 1.38 | 1.29 | 0.10 |
| Example 15 | 1.51 | 0.09 | 1.47 | 1.45 | 0.09 |
| Example 16 | 1.51 | 0.10 | 1.43 | 1.31 | 0.10 |
| Comparative Example 1 | 1.50 | 0.10 | 1.29 | 1.00 | 0.11 |

The results shown in Table 1 show that in comparison with the heat sensitive recording material of comparative example 1, the heat sensitive recording materials of examples 10 to 16 using the diazonium salt of the present invention were superior in background light-fastness and shelf stability.

Moreover, it has been confirmed that the heat sensitive recording materials of examples 10 to 16 have low color-developing density after the photo-fixing process, and are superior in the photo-fixing property.

According to the present invention, it is possible to provide a novel diazonium salt and its synthesizing method as well as a recording material using the diazonium salt, which has a fixing sensitivity to light having a wavelength of 400 to 500 nm, and is superior in photo-fixing property, raw sensitive material shelf life and background light-fastness.

What is claimed is:

1. A diazonium salt represented by the following general formula (1):

General formula (1)

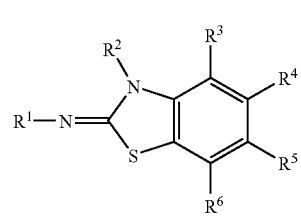

wherein in general formula (1), $R^1$ represents a hydrogen atom, an alkyl group or an aryl group; $R^2$ represents an optionally substituted alkyl group or an optionally substituted aryl group; $R^3$, $R^4$, $R^5$ and $R^6$ each independently represent a hydrogen atom, an alkyl group, an aryl group, a halogen atom, an alkoxy group, an aryloxy group, an alkyl thio group, an aryl thio group, an acyl amino group, an alkoxy carbonyl group, a carbamoyl group, a cyano group, an alkyl sulfonyl group, an aryl sulfonyl group, a sulfamoyl group, a sulfonyl amino group or $-N_2^+X^-$, and at least one of $R^3$, $R^4$, $R^5$ and $R^6$ represents $-N_2^+X^-$, in which $X^-$ represents an anion.

2. The diazonium salt according to claim 1, wherein in general formula (1), at least one of $R^1$ and $R^2$ represents an alkyl group having 1 to 30 total carbon atoms which may have a substituent, or an aryl group having 6 to 30 total carbon atoms which may have a substituent.

3. The diazonium salt according to claim 1, wherein in general formula (1), at least one of $R^1$ and $R^2$ is selected from the group consisting of an ethyl group, a butyl group, a hexyl group, a benzyl group, an N,N-diethylcarbamoylmethyl group, a 1-(N,N-dibutylcarbamoyl) ethyl group, a 1-methyl-2-phenoxyethyl group, a (4-chlorophenyl) methyl group and a (2,4-dichlorophenyl) methyl group.

4. The diazonium salt according to claim 1, wherein in general formula (1), $R^3$, $R^4$, $R^5$ and $R^6$ each independently represent a hydrogen atom, a halogen atom, an alkyl group, an aryl group, an alkoxy group, an aryloxy group, an alkyl thio group, an aryl thio group, an alkyl sulfonyl group, an aryl sulfonyl group, an acyl amino group, a sulfonyl amino group, or $-N_2^+X^-$.

5. The diazonium salt according to claim 4, wherein in general formula (1), $R^5$ represents $-N_2^+X^-$, and $R^4$ represents an alkoxy group or an aryloxy group.

6. The diazonium salt according to claim 1, wherein in general formula (1), at least one of $R^1$ to $R^6$ has a diazonio aryl group acting as a substituent.

7. A recording material comprising a support and a recording layer thereon containing a diazonium salt represented by the following general formula (1):

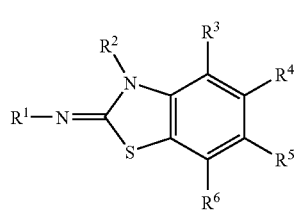

General formula (1)

wherein in general formula (1), $R^1$ represents a hydrogen atom, an alkyl group or an aryl group; $R^2$ represents an optionally substituted alkyl group or an optionally substituted aryl group; $R^3$, $R^4$, $R^5$ and $R^6$ each independently represent a hydrogen atom, an alkyl group, an aryl group, a halogen atom, an alkoxy group, an aryloxy group, an alkyl thio group, an aryl thio group, an acyl amino group, an alkoxy carbonyl group, a carbamoyl group, a cyano group, an alkyl sulfonyl group, an aryl sulfonyl group, a sulfamoyl group, a sulfonyl amino group or $-N_2^{30}X^-$, and at least one of $R^3$, $R^4$, $R^5$ and $R^6$ represents $-N_2^+X^-$, in which $X^-$ represents an anion.

8. The recording material according to claim 7, wherein recording layer is a heat sensitive recording layer and the heat sensitive recording layer further comprises a coupler.

9. The recording material according to claim 8, wherein the coupler is a compound represented by the following general formula (2) or a tautomer thereof:

$$E^1-CH_2-E^2 \qquad \text{General formula (2)}$$

wherein in general formula (2), $E^1$ and $E^2$ each independently represent an electron-attractive group, and $E^1$ and $E^2$ may be bonded to each other to form a ring.

10. The recording material according to claim 8, further comprising an organic base in the heat sensitive recording layer.

11. The recording material according to claim 10, wherein the content of the organic base is from 0.1 to 30 parts by mass per 1 mass part of the diazonium salt.

12. The recording material according to claim 8, wherein in the heat sensitive recording layer, the content of the diazonium salt represented by general formula (1) is from 0.02 to 5 g/m$^2$.

13. The recording material according to claim 8, further comprising a color-developing assistant in the heat sensitive recording layer.

14. The recording material according to claim 8, further comprising a radical generating agent in the heat sensitive recording layer.

15. The recording material according to claim 8, further comprising a vinyl monomer in the heat sensitive recording layer.

16. The recording material according to claim 8, further comprising an antioxidant in the heat sensitive recording layer.

17. The recording material according to claim 8, wherein the diazonium salt is contained in microcapsules.

18. The recording material according to claim 17, wherein capsule walls of the microcapsules contain at least one of polyurethane and polyurea as a constituent component.

19. The recording material according to claim 8, which is photo-fixed by using a light source having a light-emission center wavelength of 380 to 460 nm.

20. A method for synthesizing a diazonium salt, wherein a compound represented by the following general formula (3) is used as a raw material and is converted to a diazonium salt of the general formula (1) in the presence of an acidic solvent selected from the group consisting of sodium nitrite, potassium nitrite, nitrosyl sulfuric acid and isoamyl nitrite:

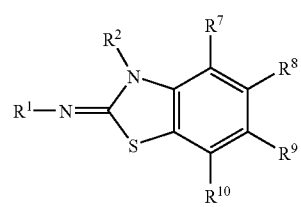

General formula (3)

wherein in general formula (3), $R^1$ represents a hydrogen atom, an alkyl group or an aryl group; $R^2$ represents an optionally substituted alkyl group or an optionally substituted aryl group; $R^7$, $R^8$, $R^9$ and $R^{10}$ each independently represent a hydrogen atom, an alkyl group, an aryl group, a halogen atom, an alkoxy group, an aryloxy group, an alkyl thio group, an aryl thio group, an acyl amino group, an alkoxy carbonyl group, a carbamoyl group, a cyano group, an alkyl sulfonyl group, an aryl sulfonyl group, a sulfamoyl group, a sulfonyl amino group or $-NHR^{11}$, and at least one of $R^7$, $R^8$, $R^9$ and $R^{10}$ represents $-NHR^{11}$, in which $R^{11}$ represents a hydrogen atom or an acyl group;

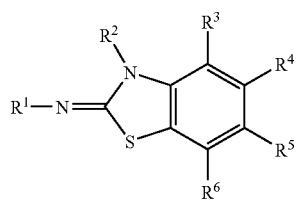

General formula (1)

wherein in general formula (1), $R^1$ represents a hydrogen atom, an alkyl group or an aryl group; $R^2$ represents an optionally substituted alkyl group or an optionally substituted aryl group; $R^3$, $R^4$, $R^5$ and $R^6$ each independently represent a hydrogen atom, an alkyl group, an aryl group, a halogen atom, an alkoxy group, an aryloxy group, an alkyl thio group, an aryl thio group, an acyl amino group, an alkoxy carbonyl group, a carbamoyl group, a cyano group, an alkyl sulfonyl group, an aryl sulfonyl group, a sulfamoyl group, a sulfonyl amino group or —$N_2^+X^-$, and at least one of $R^3$, $R^4$, $R^5$ and $R^6$ represents —$N_2^+X^-$, in which $X^-$ represents an anion.

* * * * *